(12) United States Patent
Fair et al.

(10) Patent No.: US 10,085,875 B2
(45) Date of Patent: Oct. 2, 2018

(54) SHOULDER STABILIZATION APPARATUS AND METHODS

(71) Applicant: TOP SHELF MANUFACTURING, LLC, Tracy, CA (US)

(72) Inventors: Jeffrey D. Fair, Arnold, MD (US); Robert J. McCune, Escalon, CA (US)

(73) Assignee: Top Shelf Manufacturing, LLC, Tracy, CA (US)

( * ) Notice: Subject to any disclaimer, the term of this patent is extended or adjusted under 35 U.S.C. 154(b) by 1058 days.

(21) Appl. No.: 14/299,799

(22) Filed: Jun. 9, 2014

(65) Prior Publication Data

US 2015/0351951 A1    Dec. 10, 2015

(51) Int. Cl.
    *A61F 5/37*     (2006.01)

(52) U.S. Cl.
    CPC ................... *A61F 5/3753* (2013.01)

(58) Field of Classification Search
    CPC ...... A61F 5/3715; A61F 5/3723; A61F 5/373; A61F 5/3738; A61F 5/3746; A61F 5/3753; A63B 71/08; A63B 71/12
    USPC ............................................................. 2/114
    See application file for complete search history.

(56) References Cited

U.S. PATENT DOCUMENTS

| | | | |
|---|---|---|---|
| 2,344,844 A * | 3/1944 | Baldeschwieler .... | A61F 5/3746 602/4 |
| 2,750,940 A * | 6/1956 | Fear ...................... | A61F 5/3746 602/4 |
| 4,735,198 A | 4/1988 | Sawa | |
| 2,163,450 A | 11/1992 | Cadichon et al. | |
| 5,163,450 A | 11/1992 | Cadichon et al. | |
| 5,188,587 A | 2/1993 | McGuire et al. | |
| 5,290,218 A | 3/1994 | Kilbey | |
| 5,358,470 A | 10/1994 | Johnson | |
| 5,538,015 A | 7/1996 | Paulson | |
| 5,628,725 A | 5/1997 | Ostergard | |
| 6,106,493 A | 8/2000 | Rozell | |
| 6,132,393 A | 10/2000 | Lundberg | |
| 6,306,111 B1 | 10/2001 | Dean | |
| 6,398,746 B2 | 6/2002 | Bramlage et al. | |
| 6,440,094 B1 | 8/2002 | Maas | |
| 6,709,411 B1 | 3/2004 | Olinger | |
| 7,081,101 B1 | 7/2006 | Sawa | |
| 7,255,679 B2 | 8/2007 | Ansa et al. | |
| 7,320,669 B2 | 1/2008 | Campbell et al. | |

(Continued)

FOREIGN PATENT DOCUMENTS

EP            3061428 A1 *   8/2016  .......... A61F 5/3738

OTHER PUBLICATIONS

"Donjoy Shoulder Stabilizer", DJ Orthopedics, Inc., www.djortho.com.

(Continued)

*Primary Examiner* — Kari Rodriquez
(74) *Attorney, Agent, or Firm* — Levine Bagade Han LLP

(57) ABSTRACT

Various apparatus, e.g., braces or supports, and methods for stabilizing a shoulder and/or arm of a subject are provided herein. In certain variations, a shoulder stabilization apparatus includes one or more inelastic, non-stretchable and/or rigid components which restrict or limit various types of shoulder and/or arm motion, e.g., abduction. The shoulder stabilization apparatus may include various accessory straps which restrict or limit various types of shoulder and/or arm motion.

25 Claims, 20 Drawing Sheets

(56) References Cited

U.S. PATENT DOCUMENTS

| | | |
|---|---|---|
| 7,785,281 B2 | 8/2010 | Scott |
| 8,287,478 B2 | 10/2012 | Ostergard et al. |
| 8,341,772 B1 | 1/2013 | Flores |
| 8,597,216 B2 | 12/2013 | Choudhury et al. |
| 2002/0010409 A1 | 1/2002 | Bramlage et al. |
| 2004/0193082 A1 | 9/2004 | Cofre |
| 2004/0193086 A1 | 9/2004 | Cofre |
| 2006/0167395 A1* | 7/2006 | Sawa .................. A61F 5/34 602/19 |
| 2009/0149787 A1 | 6/2009 | Scott |
| 2009/0271916 A1* | 11/2009 | Harris .................. A63B 71/12 2/456 |
| 2011/0125242 A1* | 5/2011 | Zahler .................. A61F 5/3715 607/149 |
| 2012/0041352 A1 | 2/2012 | Ostergard et al. |
| 2012/0198606 A1* | 8/2012 | Bowden ............. A41D 13/0512 2/462 |
| 2013/0317401 A1 | 11/2013 | Joslin |
| 2015/0157488 A1* | 6/2015 | Grunden .................. A61F 5/01 128/878 |

OTHER PUBLICATIONS

"Shoulder Stabilizer and Shoulder Stabilizer S.P.A,", DonJoy Orthopedics, www.donjoy.com.

"Shoulder Stabilizer", Breg Inc.

"Sully Shoulder Brace Application", DonJoy Orthopedics, donjoy.com.

* cited by examiner

SHOULDER STABILIZATION APPARATUS AND METHODS

FIELD OF THE INVENTION

The present devices and methods relate generally to apparatus, e.g., braces, supports or harnesses, and methods for stabilizing a shoulder and/or arm of a subject.

BACKGROUND

Shoulder injuries are common injuries suffered by individuals with active lifestyles. For example, many athletes participating in a variety of sports, e.g., football and hockey, suffer a variety of shoulder injuries as a result of violent collisions with other athletes, the ground and/or other objects. Due to recent rule changes in both amateur and profession football leagues regarding what constitutes a legal tackle or hit, football players are leading with their shoulders more often than in the past when applying a tackle or hit on an opponent, resulting in a greater number of shoulder injuries. While surgery may be ultimately performed to repair the damaged joint or muscle, surgery is not ideal or practical during the middle of a season or even during the career of an athlete, where repeated hitting and tackling is likely to reinjure the repaired shoulder. Therefore, an individual may wear a support to temporarily stabilize the shoulder and prevent further injury.

While various shoulder supports exist, these supports have many limitations and undesirable features. For example, many existing supports are rigid and don't allow for sufficient flexibility or movement by the wearer, so the wearer cannot continue to effectively participate in an athletic activity and perform the required movements while maintaining their shoulder in a safe and stabilized position to prevent further injury. Many existing supports unnecessarily or overly restrict movement of a wearer, making it difficult or impossible to continue to participate in an athletic or other activity while wearing the support. Also, many existing supports are not breathable, lacking breathable fabrics or materials, making the wearer hot, and many are bulky or cumbersome, making them uncomfortable to wear during an activity for any extended period of time. Many existing supports are very difficult to put on, often requiring the assistance of another individual and taking significant time to adequately secure the supports to a wearer.

As a result of the above limitations, there is a need for an improved apparatus and method for stabilizing the shoulder and/or arm of a subject that minimizes or eliminates such limitations or restrictions.

BRIEF SUMMARY

Various devices and methods for stabilizing a subject's shoulder are described herein.

In certain variations, a shoulder stabilization apparatus is provided. The apparatus includes a torso portion having a neck opening, a side opening, a side wrap and an inelastic and/or non-stretchable torso segment surrounding a bottom periphery of the torso portion. The apparatus includes an arm sleeve extending from the torso portion, wherein the arm sleeve has an inelastic and/or non-stretchable end segment, the arm sleeve being configured to receive a subject's arm, the arm extending from an affected or target shoulder. An inelastic and/or non-stretchable axillary segment forms an integrated connection between the inelastic and/or non-stretchable torso segment and the inelastic and/or non-stretchable arm sleeve end segment which limits abduction and/or external rotation of the subject's affected or target shoulder and/or arm.

The apparatus may also include an arm strap having a first end configured to be removably fastened to a posterior portion of the arm sleeve. The arm strap extends across an anterior portion of the torso portion and has a second end configured to be adjustably coupled to a coupling component located on the side wrap such that the arm strap limits abduction and/or external rotation of the subject's affected or target shoulder and/or arm.

The apparatus may also include a back strap. The back strap has a first end configured to be removably fastened to a posterior portion of the torso portion. The back strap extends across a posterior portion of the torso portion and has a second end configured to be adjustably coupled to a coupling component located on the inelastic and/or non-stretchable axillary segment, such that the back strap limits forward flexion and/or adduction of the subject's affected or target shoulder and/or arm.

The apparatus may also include a shoulder strap. The shoulder strap has a first end configured to be removably fastened to a posterior portion of the torso portion above the affected or target shoulder. The shoulder strap has a bifurcated second end having a first elongated segment which is configured to be adjustably coupled to a coupling component located on the side wrap, and a second truncated segment which is configured to be adjustably coupled to a top surface of the first elongated segment. The shoulder strap extends across an anterior portion of the torso portion, such that the shoulder strap provides support to the AC joint, restricts AC separation and/or provides compression of the rotator cuff of a subject's affected or target shoulder.

Various methods for stabilizing a shoulder and for utilizing the shoulder stabilization apparatus to stabilize a subject's shoulder are also described herein.

DETAILED DESCRIPTION

Figure 1:
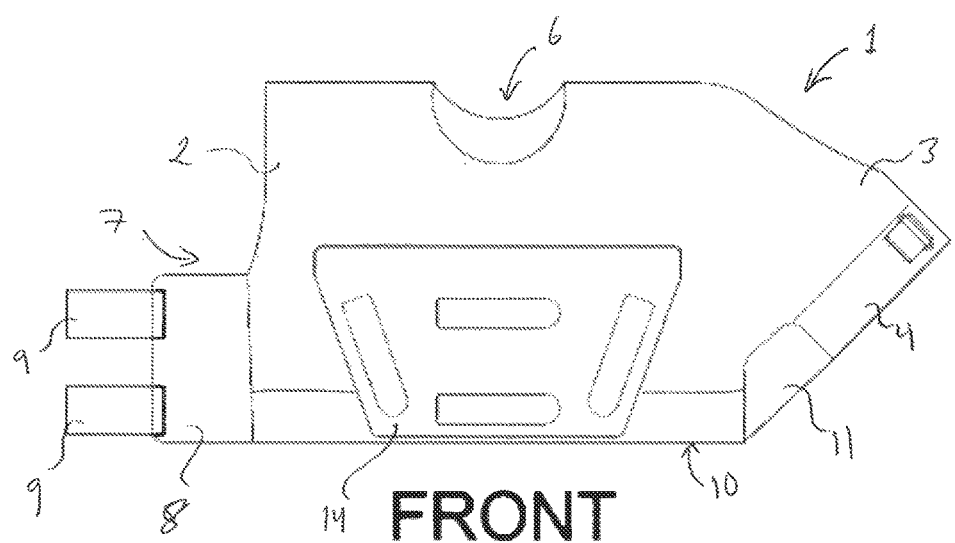
FIG. 1 illustrates a front view of a variation of a shoulder stabilization apparatus in an open position.

Variations of the devices are best understood from the detailed description when read in conjunction with the accompanying drawings. It is emphasized that, according to common practice, the various features of the drawings may not be to-scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

In certain variations, a shoulder stabilization apparatus, e.g., a shoulder stabilization brace or support is provided. The shoulder stabilization apparatus includes a torso portion. The torso portion may have a neck opening for receiving a subject's head and/or neck. A side opening on the torso portion allows the torso portion to receive at least a portion of the subject's torso or body, such that the torso portion may be positioned or slipped on or around the subject's torso or body. The torso portion may surround the torso, e.g., covering the entire or at least a portion of the torso. For example, the torso portion may extend varying longitudinal lengths of the subject's torso, e.g., extending from the neck to the waist or pelvis, or to an area above the waist or pelvis, or covering the thorax and abdomen or at least a portion thereof. It may cover at least a portion of or the entire affected or targeted shoulder along with the arm sleeve (discussed below) and/or it may cover at least a portion of or the entire unaffected or non-targeted shoulder. The torso portion may cover the torso or body like a shirt or garment.

The torso portion may include a side wrap or side extension, which wraps around the side of the subject's torso and connects to an anterior portion or segment, e.g., to an attachment panel, of the torso portion. In certain variations, the attachment panel may include a fastening component, e.g., a hook or loop fastener. The attachment panel may be constructed of a stiffer or more rigid material compared to the rest of the torso portion. Optionally, the attachment panel may be constructed of an inelastic and/or non-stretchable material, and include one or more inserts, which provide a rigidity to prevent the apparatus from migrating up on the torso of a subject.

The side wrap may include one or more closure straps. The closure straps may have a first end affixed to the side wrap and a second end, which may be removably fastened or attachable to an anterior portion or segment of the torso portion, to close the side opening of the torso portion and to secure the torso portion to the subject.

The side opening may be located on the side of the shoulder stabilization apparatus, opposite the arm sleeve (discussed below). In other variations, the side opening may be located below the arm sleeve. Optionally, the shoulder stabilization apparatus may include multiple side openings, one on each side of the apparatus. In other variations, an opening may be located on the back of the apparatus in addition to or instead of the side of the apparatus to facilitate placement of the apparatus of a subject's body.

The torso portion may also include an inelastic and/or non-stretchable torso segment, e.g., a torso strip. The inelastic and/or non-stretchable torso segment may surround at least a portion of the bottom periphery of the torso portion or the entire periphery or substantially the entire periphery. The inelastic and/or non-stretchable torso segment may surround an inner surface of the bottom periphery of the torso portion. Optionally, the inelastic and/or non-stretchable torso segment may include a gripping or adhesive surface to prevent or limit sliding or unwanted movement of the torso portion and shoulder stabilization apparatus along or on a torso of the subject, e.g., in a vertical or horizontal direction relative to the subject's body.

The shoulder stabilization apparatus includes one or more arm sleeves, which extend from the torso portion. The arm sleeve may include at least one inelastic and/or non-stretchable distal end segment or portion. The inelastic and/or non-stretchable end segment may surround at least a portion of or the entire arm sleeve or an opening of the arm sleeve. Optionally, the inelastic and/or non-stretchable end segment may include a gripping or adhesive surface to prevent or limit sliding or unwanted movement of the arm sleeve along, on or around the arm of the subject. The arm sleeve is configured to receive a subject's arm. The arm extending from an affected shoulder of the subject is inserted through an opening in the arm sleeve, and received by the arm sleeve. The arm sleeve may extend along at least a portion of the bicep or cover at least a portion of the bicep.

The arm sleeve may be adjustable to accommodate a variety of arm sizes. For example, the arm sleeve may include an adjustable slit or gap at its distal end, where the slit or gap is adjacent to the opening at the distal end of the arm sleeve. The arm sleeve may also include one or more arm sleeve fasteners. The arm sleeve fasteners may have a first end, which is affixed to the arm sleeve, on a first side of the slit or gap, and a second end, which may be removably fastened or attachable to the arm sleeve, on a second side of the slit or gap. The arm sleeve fastener may be fastened or attached across the slit or gap at varying lengths (depending on the position of the second end of the arm sleeve fastener). As a result, the diameter or width of the slit or gap may be increased or decreased, and the size of the arm sleeve opening may be increased or decreased to accommodate the particular arm positioned therein.

The shoulder stabilization apparatus also includes one or more inelastic and/or non-stretchable axillary segments or portions positioned between the arm sleeve and the inelastic and/or non-stretchable torso segment. For example, the axillary segment may extend across the axilla or armpit or underarm region, bridging from the bottom end of the torso portion to the distal end of the arm sleeve. The inelastic and/or non-stretchable axillary segment forms an integrated connection between the inelastic and/or non-stretchable end segment of the arm sleeve and the inelastic and/or non-stretchable torso segment. The inelastic and/or non-stretchable torso segment, axillary segment and end segment of the arm sleeve may be separate components, which when connected, e.g., via stitching, sewing, or other attachment or coupling methods or features, form an integrated unit or segment that limits or restricts abduction and/or external rotation of the subject's affected shoulder and/or arm when the shoulder stabilization apparatus is positioned or secured on a subject. The inelastic and/or non-stretchable torso segment and the inelastic and/or non-stretchable end segment of the arm sleeve are adjustable to accommodate various torso and arm sizes, and to position and secure the shoulder stabilization apparatus on a subject in a manner that provides a customized fit for the particular subject wearing the shoulder stabilization apparatus to accommodate the specific dimensions of the subject and to provide the desired degree of shoulder and/or arm stabilization and restriction of shoulder and/or arm motion. Once the torso segment and the end segment of the arm sleeve are secured and fastened to the desired tension, the inelastic and/or non-stretchable segments of the shoulder stabilization apparatus, i.e., the torso segment, end segment of the arm sleeve and axillary segment work in unison to restrict motion of the subject's affected shoulder, i.e., abduction of the affected shoulder and/or arm, to stabilize the shoulder and/or arm and to prevent injury or to prevent further injury.

For example, in certain variations, the inelastic, non-stretchable or rigid segments or components of the shoulder stabilization apparatus, i.e., the torso segment, axillary segment and end segment of the arm sleeve, act in unison to limit or restrict abduction of a user's affected arm and/or shoulder, where abduction starts to be restricted or limited when the arm reaches about a 30 degree angle relative to the vertical mid-line of a subject. In certain variations, abduction motion starts to be restricted or limited when the arm reaches about a 45 degree angle relative to the vertical mid-line of a subject. In other variations, abduction motion is restricted or limited when the arm reaches about a 45 to 90 degree angle relative to the vertical mid-line of a subject. In certain variations, such a restriction or limitation of abduction motion or external rotation may be achieved without the use of a separate arm, back or shoulder strap.

The three inelastic and/or non-stretchable segments, the torso segment, axillary segment and end segment of the arm sleeve described supra may be provided as three separate components, which are integrated or connected to achieve the desired functionality of shoulder and/or arm motion restriction. Utilizing three separate components or pieces which are then integrated or connected provides advantages with respect to ease of manufacturing.

In other variations, a single inelastic and/or non-stretchable segment or strip may extend around the bottom periphery of the torso portion, along the axilla and around the end of the arm sleeve, making up an inelastic and/or non-stretchable torso segment, inelastic and/or non-stretchable axillary segment and an inelastic and/or non-stretchable arm sleeve end portion. This configuration also acts to restrict abduction and/or external rotation of the shoulder and/or arm of the subject on which the shoulder stabilization apparatus is positioned and secured.

The inelastic and/or non-stretchable segments or components of the shoulder stabilization apparatus described herein may be completely or partially inelastic and/or non-stretchable or at least partially inelastic and/or non-stretchable.

The torso portion and arm sleeve may include or be made entirely or at least partially from a stretchable, elastic, light weight and breathable material to provide comfort, and movability to the subject wearing the shoulder stabilization apparatus and to conform to the subject's body. The elastic, stretchable and/or dynamic properties of certain portions of the shoulder stabilization apparatus allow the subject to still have a certain degree of mobility while wearing the shoulder stabilization apparatus, allowing them to safely partake and compete in activities, e.g., athletic activities such as football or hockey, while wearing the shoulder stabilization apparatus. The breathable and elastic materials are combined with non-stretch or inelastic and/or non-slip materials (e.g., such materials are used to create the inelastic and/or non-stretchable torso segment, inelastic and/or non-stretchable axillary segment and inelastic and/or non-stretchable arm sleeve end segment) to provide a contoured fit to a variety of shapes and sizes of subjects while providing the combined torso and arm control needed when addressing a shoulder instability. A variety of materials having elastic and/or inelastic and/or non-stretchable or rigid properties or characteristics may be utilized in the shoulder stabilization apparatus. Examples of materials used to construct the elastic or stretchable portions of the shoulder stabilization apparatus include but are not limited to, neoprene, nylon, elastic, or lycra and other suitable materials. Materials used to construct the inelastic and/or non-stretchable segments discussed supra include materials having inelastic or non-stretch properties or materials sewn or constructed in an inelastic or non-stretch manner.

The shoulder stabilization apparatus may include one or more accessories or straps. For example, the shoulder stabilization apparatus may include one or more arm straps, one or more shoulder straps and/or one or more back straps for controlling or limiting movement of the subject's shoulder and/or arm and/or for stabilizing the subject's shoulder.

An arm strap may include a first end, which may be removably fastened or attachable or anchored to a posterior portion of the arm sleeve. The arm strap may include a second end, which may be adjustably coupled to at least one coupling component, e.g., a buckle or D-ring, located on the side wrap or other area of the torso portion. The arm strap is fastened to the posterior portion of the arm sleeve (e.g., to a fastening component or patch), extends across the anterior or front portion of the torso portion, and is coupled or attached to the coupling component on the side wrap or other area of the torso portion e.g., on an anterior portion of the torso portion or on a front panel of the torso portion, e.g., on a side of the torso opposite the affected or target shoulder. The tension or length of the arm strap may be adjusted to provide the desired degree of motion control, restriction, or limitation, depending on the particular subject's needs. The second end of the arm strap may be looped through the coupling component and folded back on itself to be fastened or attached to the arm strap or the torso portion. Once in position, the arm strap limits or restricts abduction and/or horizontal abduction and/or external and/or internal rotation of the subject's affected shoulder and/or arm and/or helps stabilize the shoulder.

A back strap may include a first end, which may be removably fastened or attachable or anchored to a posterior portion of the torso portion (e.g., below the axilla of the unaffected or target arm or shoulder or on a lower portion of the posterior or back portion of the torso portion). The back strap may include a second end, which may be adjustably coupled to at least one coupling component, e.g., a buckle or D-ring, located on or adjacent to the inelastic and/or non-stretchable axillary segment. The back strap is fastened to the posterior portion of the torso portion (e.g., to coupling component or buckle), extends across the posterior or back portion of the torso portion, and is coupled or attached to the coupling component on or adjacent to the inelastic and/or non-stretchable axillary segment or other area or posterior area of the torso portion, e.g., on a side of the torso opposite the portion where the first end of the back strap is attached. The tension or length of the back strap may be adjusted to provide the desired degree of motion control, restriction or limitation, depending on the particular subject's needs. The second end of the back strap may be looped through the coupling component and folded back on itself to be fastened or attached to the back strap or the torso portion. Once in position, the back strap limits or restricts forward flexion, adduction and/or horizontal abduction or adduction of the subject's affected shoulder and/or arm and/or helps stabilize the shoulder.

The shoulder stabilization apparatus may also include one or more anchoring straps for securely fastening the arm strap to the arm sleeve. The anchoring strap may have a first end affixed to a posterior portion of the arm sleeve and a second end, which may be removably fastened or attachable to the arm strap. The second end of the anchoring strap may be pulled away from the posterior portion of the arm sleeve, and the first end of the arm strap can be positioned between the posterior portion of the arm sleeve and the underside of the anchoring strap. The anchoring strap is fastened to the top surface of the first end of the arm strap to provide a secure fastening of the arm strap to the arm sleeve, sandwiching the arm strap between the anchor strap and the arm sleeve.

In another variation of the shoulder stabilization apparatus, in addition to the arm strap and back strap described above, a shoulder stabilization device may include one or more shoulder straps (described in more detail below). In certain variations, the shoulder stabilization device may include a shoulder strap in addition to the arm and/or back straps, or without the arm and/or back straps. A shoulder stabilization apparatus may be utilized without the arm strap, back strap or shoulder strap, e.g., where motion restriction or limitation is provided solely via the rigid or inelastic and/or non-stretchable torso segment, axillary segment and/or arm sleeve end segment of the torso portion and arm sleeve, or it may be utilized with any one of the straps or any combination of the straps to provide customized shoulder and/or arm stabilization for a particular subject depending on their needs and particular condition. For example, abduction may be restricted or limited by a combination of the inelastic and/or non-stretchable segments of the torso portion and the arm strap when worn by a subject. The shoulder stabilization apparatus, including the torso portion and various straps, may be used to stabilize or prevent a shoulder dislocation or subluxation.

In certain variation, the shoulder stabilization apparatus includes a torso portion. The torso portion may have a neck opening for receiving a subject's head and/or neck. A side opening on the torso portion allows the torso portion to receive at least a portion of the subject's torso or body, such that the torso portion may be positioned on or around the subject's torso or body. The torso portion may include a side wrap or side extension, which wraps around the side of the subject's torso and connects to an anterior portion or segment, e.g., to an attachment panel, of the torso portion.

The side wrap may include one or more closure straps. The closure straps may have a first end affixed to the side wrap and a second end, which may be removably fastened or attachable to an anterior portion or segment of the torso portion, to close the side opening of the torso portion and to secure the torso portion to the subject.

The torso portion may also include an inelastic and/or non-stretchable torso segment, e.g., a torso strip. The inelastic and/or non-stretchable torso segment may surround at least a portion of the bottom periphery of the torso portion. The inelastic and/or non-stretchable torso segment may surround an inner surface of the bottom periphery of the torso portion. Optionally, the inelastic and/or non-stretchable torso segment may include a gripping or adhesive surface to prevent or limit sliding or unwanted movement of the torso portion and shoulder stabilization apparatus along or on a torso of the subject, e.g., in a vertical or horizontal direction relative to the subject's body.

The shoulder stabilization apparatus includes one or more arm sleeves, which extend from the torso portion. The arm sleeve may include an inelastic and/or non-stretchable distal end segment. Optionally, the inelastic and/or non-stretchable distal end segment may include a gripping or adhesive surface to prevent or limit sliding or unwanted movement of the arm sleeve along, on or around the arm of the subject. The arm sleeve is configured to receive a subject's arm. The arm extending from an affected shoulder of the subject is inserted through an opening in the arm sleeve, and received by the arm sleeve.

The arm sleeve may be adjustable to accommodate a variety of arm sizes. For example, the arm sleeve may include an adjustable slit or gap at its distal end, where the slit or gap is adjacent to the opening at the distal end of the arm sleeve. The arm sleeve may also include one or more arm sleeve fasteners. The arm sleeve fasteners may have a first end, which is affixed to the arm sleeve, on a first side of the slit or gap, and a second end, which may be removably fastened or attachable to the arm sleeve, on a second side of the slit or gap. The arm sleeve fastener may be fastened or attached across the slit or gap at varying lengths (depending on the position of the second end of the arm sleeve fastener). As a result, the diameter or width of the slit or gap may be increased or decreased, and the size of the arm opening may be increased or decreased to accommodate the particular arm positioned therein.

The shoulder stabilization apparatus also includes one or more inelastic and/or non-stretchable axillary segments positioned between the arm sleeve and the inelastic and/or non-stretchable torso segment. The inelastic and/or non-stretchable axillary segment forms an integrated connection between the inelastic and/or non-stretchable end segment of the arm sleeve and the inelastic and/or non-stretchable torso segment. The torso segment, axillary segment and end segment of the arm sleeve may be separate components, which when connected, form an integrated unit or segment that limits or restricts abduction and/or external rotation of the subject's affected shoulder and/or arm when the shoulder stabilization apparatus is positioned or secured on a subject. In other variations, a single inelastic and/or non-stretchable segment or strip may extend around the bottom periphery of the torso portion, along the axilla (e.g., the arm pit or under arm region) and around the end of the arm sleeve. This configuration also acts to restrict abduction and/or external rotation of the shoulder and/or arm of the subject on which the shoulder stabilization apparatus is positioned and secured.

In certain variations, such restriction or limitation of abduction motion or external rotation may be achieved without the use of a separate arm, back or shoulder strap.

The shoulder stabilization apparatus includes one or more shoulder straps having a first end which may be removably fastened or attachable or anchored to a posterior portion of the torso portion, e.g., above, on or near the affected shoulder. The shoulder strap may include a bifurcated second end. The bifurcated second end includes a first elongated segment which may be adjustably coupled to at least one coupling component, e.g., a buckle or D-ring, located on the side wrap or other area of the torso portion, e.g., on an anterior portion or front panel of the torso portion. The bifurcated second end also includes a second truncated segment which may be adjustably fastened or coupled to a top surface of the first elongated segment. The bifurcated shoulder strap is fastened to the posterior portion of the torso portion (e.g., to a fastening component or patch). The first elongated segment extends across the anterior or front portion of the torso portion, and is coupled or attached to the coupling component on the side wrap or other area or anterior area of the torso portion, e.g., on a side of the torso opposite the affected or target shoulder. The tension or length of the first elongated segment may be adjusted to provide the desired degree of motion control, restriction, limitation, support or compression depending on the particular subject's needs. The first elongated segment may be looped through the coupling component and folded back on itself to be fastened or attached to the first elongated segment or the torso portion. The second truncated segment is fastened or coupled to the top surface of the first elongated element to capture or contour the strap around the affected area of the shoulder. For example, the second truncated segment may be folded or wrapped over the base of the first elongated segment to conform or contour the strap to the affected or target area of the shoulder. Once in position, the shoulder strap conforms or contours to the affected area of the subject's shoulder, and provides support to the AC joint, restricts AC separation and/or provides compression or support of the rotator cuff of a subject's affected shoulder and/or stabilizes the shoulder or prevents or stabilizes a shoulder dislocation or subluxation.

The shoulder stabilization apparatus may also include one or more anchoring straps for securely fastening the shoulder strap to the torso portion. The anchoring strap may have a first end affixed to a posterior portion of the torso portion and a second end, which may be removably fastened or attachable to the shoulder strap. The second end of the anchoring strap may be pulled away from the posterior portion of the torso portion, and the first end of the shoulder strap can be positioned between the posterior portion of the torso portion and the underside of the anchoring strap. The anchoring strap is fastened to the top surface of the first end of the shoulder strap to provide a secure fastening of the shoulder strap to the torso portion, sandwiching the shoulder strap between the anchor strap and the torso portion.

Figure 15:
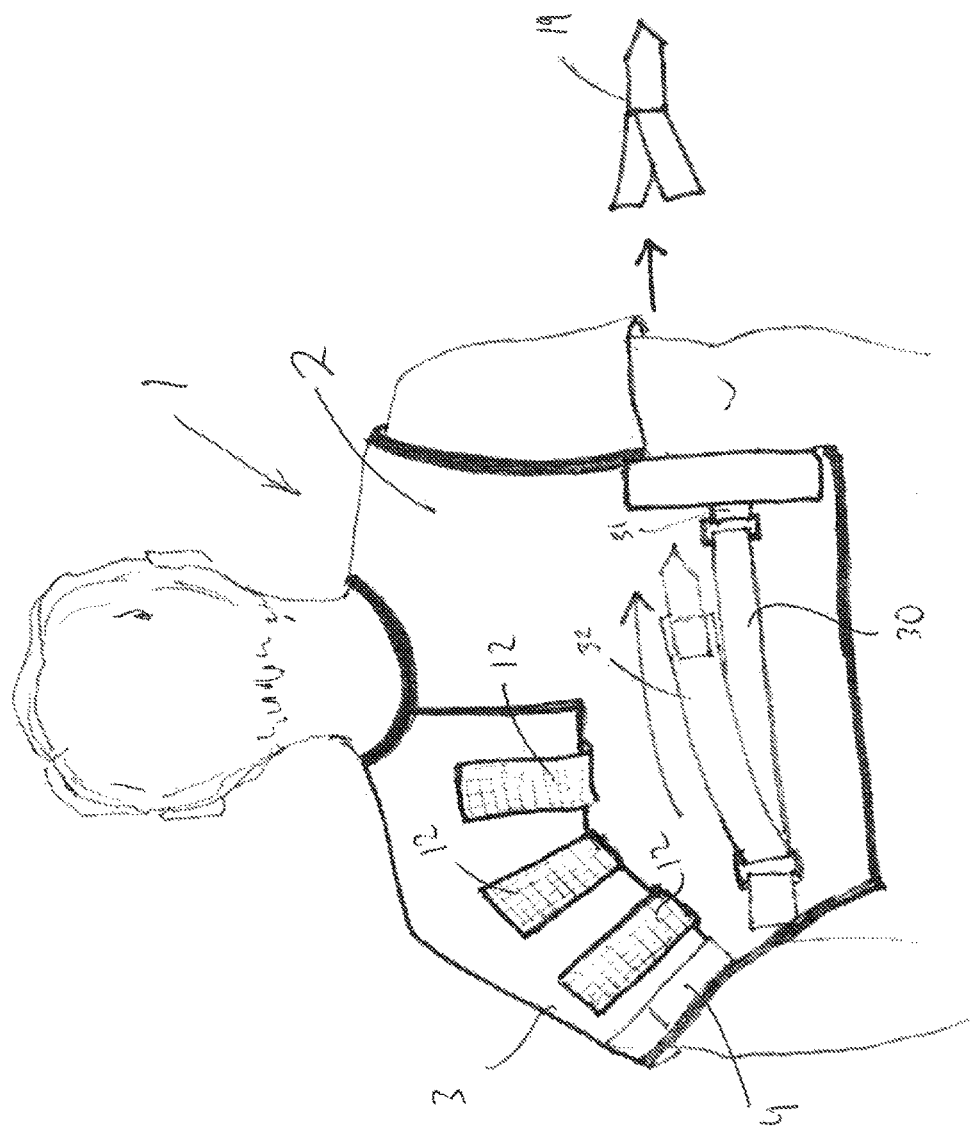
Figure 16:
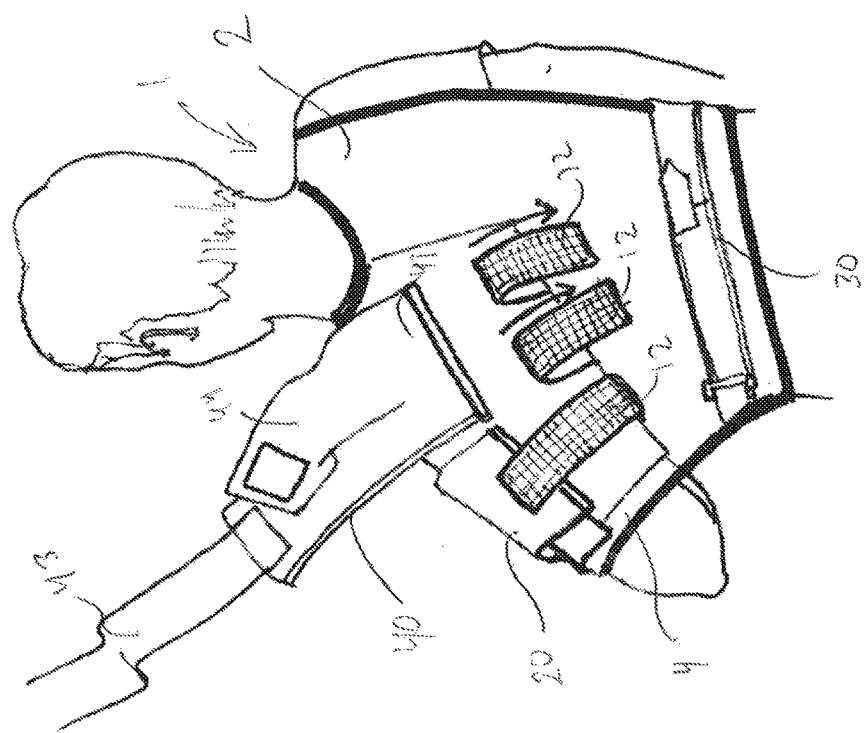
Figure 17:
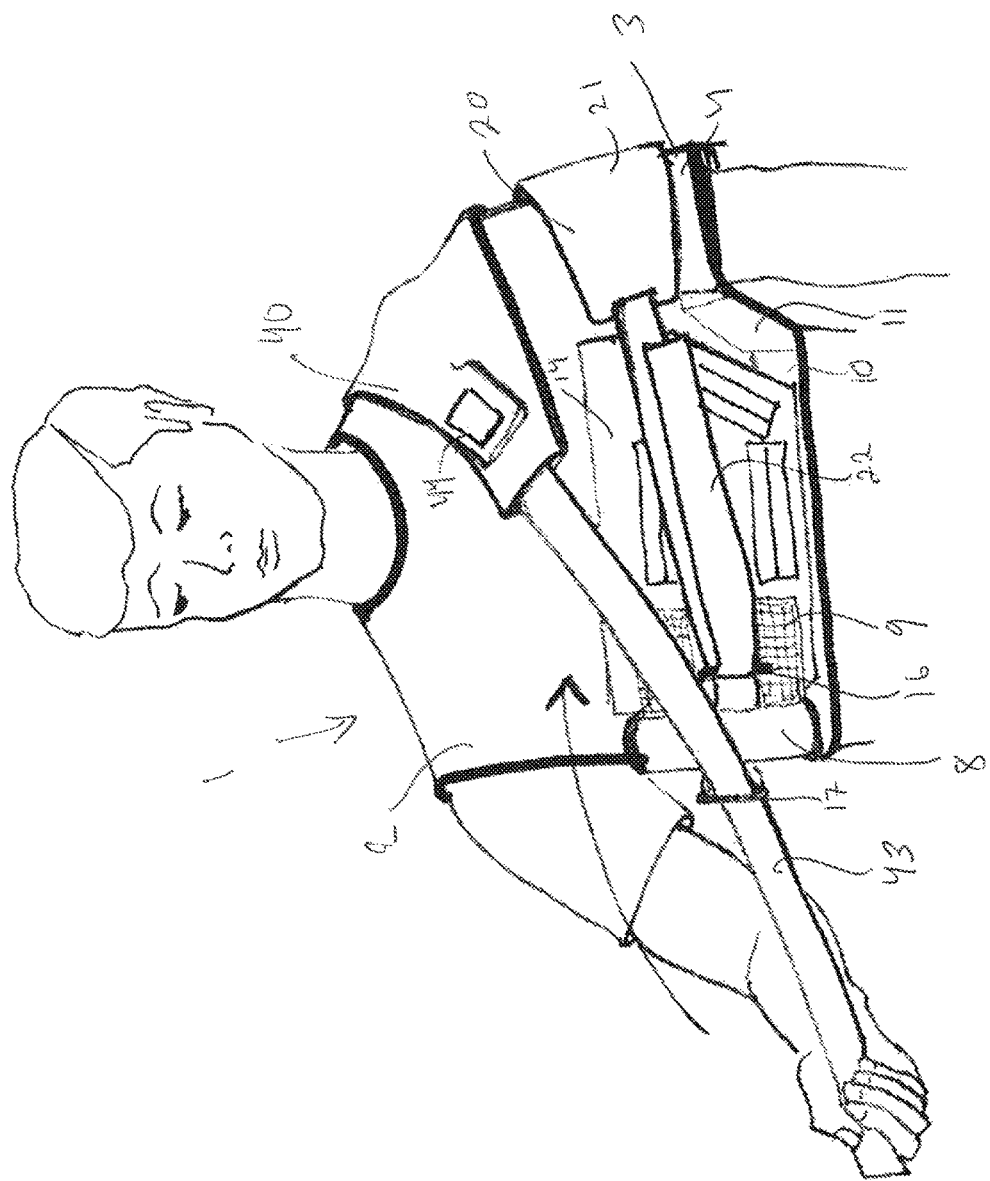
Figure 18:
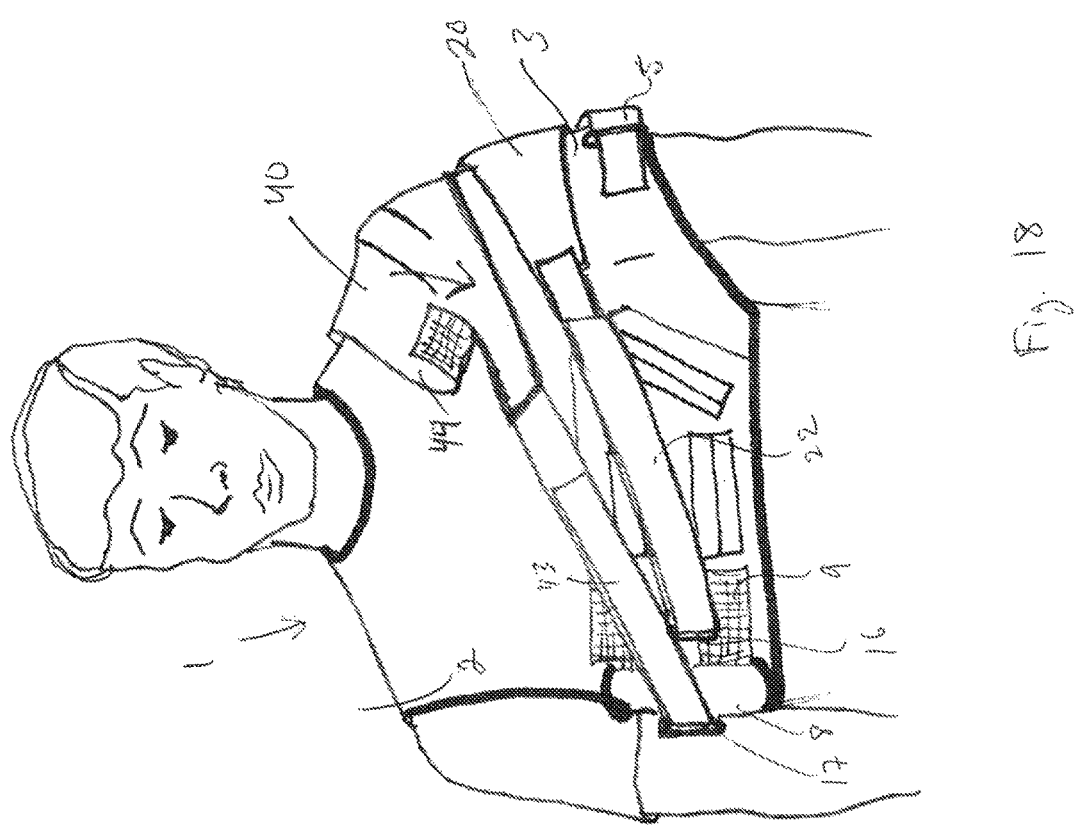

Any of the straps or other components described herein may include one or more fastening components to fasten the strap or other components on the shoulder stabilization apparatus. A fastening component may include any fastener or attachment mechanism known in the art. For example, a fastening component may include a hook and loop fastener (e.g., Velcro®) or an adhesive. For example, the arm strap may have a hook or loop fastener at its first end, which will fasten to a hook or loop fastener positioned on a posterior portion of the arm sleeve. The arm strap may have a hook or loop fastener at its second end, which will fasten to a hook or loop fastener located on another portion of the arm strap or on the anterior or front portion of the torso portion. The back and shoulder straps, arm sleeve fasteners, anchor straps and closure straps may have similar hook or loop fasteners or other adhesives. Any of the straps or fasteners may optionally include removable fastening components, which can be positioned or repositioned on various spots along a particular strap or fastener to provide even more adjustment options and to accommodate different sizes, dimensions, needs and conditions of a particular subject. Optionally, an "alligator" or "y" tab 19 (See, e.g., FIG. 15) can be applied to a strap after cutting or adjusting a strap to a desired length, and a fastening component may be attached to the tab. Any of the straps described herein may be length adjustable.

In certain variations of the shoulder stabilization apparatus, the arm strap and/or shoulder strap may extend only across the anterior portion or front of the torso portion without extending across the posterior portion or back of the torso portion and/or without encircling or wrapping completely around a subject's arm. Similarly, the back strap may extend only across the posterior portion or back of the torso portion without extending across the anterior portion or front of the torso portion and/or without encircling or wrapping completely around a subject's arm.

The shoulder stabilization apparatus, including the accessory straps may be positioned and secured on a subject by the subject alone without the assistance of a second person. Optionally, a second person may assist the subject with positioning and securing the shoulder stabilization apparatus, and one or more of the straps on the subject.

In certain variations, the arm strap may be at least partially inelastic and/or non-stretchable, and/or at least a portion of the arm strap may be elastic, dynamic or stretchable to provide give or to conform to a body part of the subject. This allows for a certain amount of external and/or internal rotation and/or abduction of the subject's affected shoulder and/or arm, even when the arm strap is in place and securely fastened to the torso portion on the subject.

In certain variations, the back strap may be at least partially inelastic and/or non-stretchable. In other variations, at least a portion of the back strap may be elastic, dynamic or stretchable to provide give or to conform to a body part of the subject. This allows for a certain amount of forward flexion and adduction of the subject's affected shoulder and/or arm, even when the back strap is in place and securely fastened to the torso portion on the subject.

In certain variations, the shoulder strap may be at least partially inelastic and/or non-stretchable, and/or at least a portion of the shoulder strap may be elastic, dynamic or stretchable to provide give or to conform or contour to the affected area of the subject's shoulder. This allows for a certain amount of movement of the subject's affected shoulder and/or arm, even when the shoulder strap is in place and securely fastened to the torso portion on the subject.

In other variations, the entire accessory arm strap and/or shoulder strap may be flexible or stretchable.

The elastic, stretchable and/or dynamic properties of the accessory straps allow the straps to give and flex, so there is not a hard stop of the subject's movement but a gradual restriction or dampening of the subject's movement. This also allows the subject to still have a certain degree of mobility while wearing the shoulder stabilization apparatus, allowing them to safely partake and compete in activities, e.g., athletic activities such as football or hockey, while wearing the shoulder stabilization apparatus.

A variety of materials having elastic or stretchable, or inelastic, non-stretchable or rigid properties or characteristic may be utilized in the accessory straps of the shoulder stabilization apparatus. Examples of materials used to construct the elastic or stretchable portions of the accessory straps include but are not limited to neoprene, elastic, or lycra and other suitable materials. Examples of materials used to construct the inelastic, non-stretchable or rigid portions of the accessory straps include but are not limited to webbing or non-stretch hook and loop and materials having inelastic or non-stretch properties or materials sewn or constructed in an inelastic or non-stretch manner.

Examples of types of motions (one or more of) that may be restricted or limited by the shoulder stabilization apparatus and/or accessory straps to various degrees include but are not limited to the following:

Abduction, which may refer to movement of a limb or joint away from the midline or axis of the body, e.g., movement of an arm or shoulder away from the midline or longitudinal axis of the body. The shoulder stabilization apparatus may limit or restrict abduction, i.e., limit the degree to which the subject wearing the apparatus can move their arm or affected shoulder away from the midline of their body.

Adduction, which may refer to movement of a limb or joint toward the midline or axis of the body, e.g., movement of an arm or shoulder toward the midline or longitudinal axis of the body. The shoulder stabilization apparatus may limit or restrict adduction, i.e., limit the degree to which the subject wearing the apparatus can move their arm or affected shoulder toward the midline of their body.

Horizontal abduction, which may refer to the movement of the arms from horizontally across the body. Starting from a position where the arms are straight to the front (e.g., shoulders flexed at 90 degrees), moving in the transverse plane to end in a position where the arms are straight out to the side (e.g., flexed at 90 degrees).

Forward flexion, which may refer to a forward raising of the arm by a movement at the shoulder.

Extension, which may refer to a rearward swinging of the arm by a movement at the shoulder.

External rotation, which may refer to a movement at a joint that causes rotation of a limb or part of a limb around its long axis away from the midline of the body.

Internal rotation, which may refer to a movement at a joint that causes rotation of a limb or part of a limb around its long axis toward the midline of the body.

The variations of shoulder stabilization apparatus described herein may be adjustable to accommodate a variety of shapes and sizes, and the may be designed such that the cover a range of sizes, e.g., small to medium or medium to large.

Various Examples of a Shoulder Stabilization Apparatus are Illustrated in the Figures Included Herein.

FIGS. 1-2 & 5-6 illustrate front and back views of one variation of a unilateral shoulder stabilization apparatus 1 in an opened and a closed position. Shoulder stabilization apparatus 1 includes a torso portion 2. The torso portion 2 includes a neck opening 6 for receiving a subject's head and/or neck. A side opening 7 in the torso portion 2 allows the torso portion 2 to receive at least a portion of the subject's torso or body, such that the torso portion 2 may be positioned on or around the subject's torso or body. The torso portion 2 includes a side wrap 8 or side extension, which wraps around the side of the subject's torso and connects to an attachment panel 14 located on the anterior or front portion of the torso portion 2.

Figure 5:
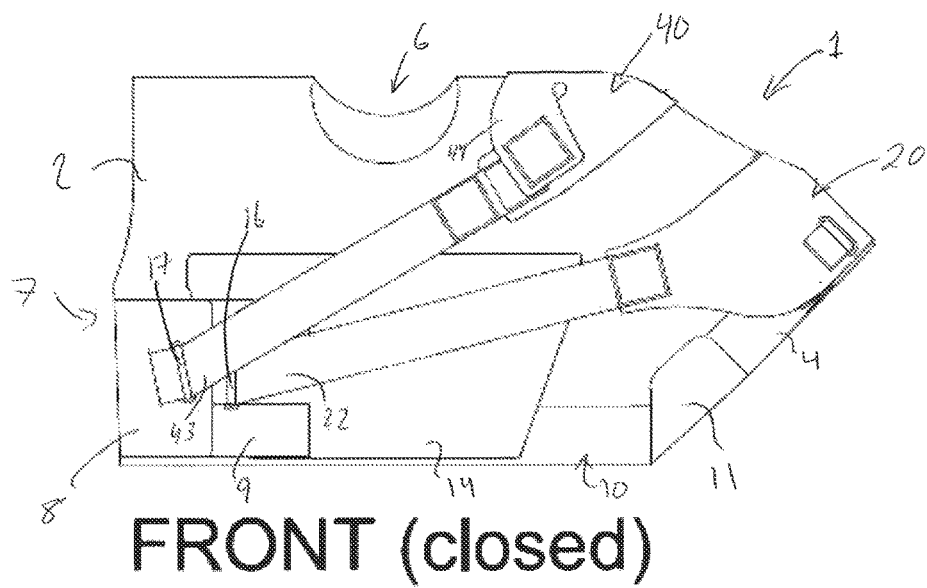
FIG. 5 illustrates a front view of a variation of a shoulder stabilization apparatus in a closed position with an arm strap and shoulder strap secured thereto.

The side wrap 8 includes one or more, e.g., two, closure straps 9. The closure straps 9 have a first end affixed to or extending from the side wrap 8 and a second end which includes a fastening component, e.g., a hook or loop fastener. As shown in FIG. 5, the second end of the closure straps 9 are fastened or attached, via the fastening component, to a fastening component, e.g., hook or loop fastener, located on the attachment panel 14 on the anterior portion of the torso portion 2. This closes the side opening 7 of the torso portion 2 and secures the torso portion 2 to the subject.

The torso portion 2 may also include an inelastic and/or non-stretchable or rigid torso segment, portion or strip 10. The inelastic torso segment 10 may surround at least a portion of the bottom periphery of the torso portion 2. For example, the inelastic torso segment 10 may surround an inner surface of at least a portion of the bottom periphery of the torso portion 2. Optionally, the inelastic torso segment 10 may include a gripping or adhesive surface to prevent or limit sliding or unwanted movement of the torso portion 2 and shoulder stabilization apparatus along or on a torso of the subject, e.g., in a vertical or horizontal direction relative to the subject's body.

The shoulder stabilization apparatus 1 includes an arm sleeve 3, which extends from the torso portion 2. The arm sleeve 3 may include an inelastic and/or non-stretchable or rigid distal end segment, strip or portion 4. Optionally, the inelastic distal end segment 4 may include a gripping or adhesive surface to prevent or limit sliding or unwanted movement of the arm sleeve along, on or around the arm of the subject. The arm sleeve 3 is configured or sized to receive a subject's arm. The arm extending from an affected shoulder of the subject is inserted through an opening in the arm sleeve 3, and received by the arm sleeve 3.

The arm sleeve 3 may be adjustable to accommodate a variety of arm sizes. For example, the arm sleeve 3 may include an adjustable slit or gap (not shown) at its distal end, where the slit or gap is adjacent to the opening at the distal end of the arm sleeve 3. The arm sleeve 3 also includes one or more arm sleeve fasteners 5. The arm sleeve fastener 5 has a first end, which is affixed to the arm sleeve 3 on a first side of the slit or gap, and a second end, which is removably fastened or attachable to the arm sleeve 3, on a second side of the slit or gap. The arm sleeve fastener 5 may be fastened or attached across the slit or gap at varying lengths (depending on the position of the second end of the arm sleeve fastener 5). As a result, the diameter or width of the slit or gap may be increased or decreased, and the size of the arm sleeve opening may be increased or decreased to accommodate the size of the particular arm positioned therein.

The shoulder stabilization apparatus 1 also includes an inelastic and/or non-stretchable or rigid axillary segment or portion 11 positioned between the arm sleeve 3 and the inelastic torso segment 10. The inelastic axillary segment 11 forms an integrated connection between the inelastic end segment 4 of the arm sleeve 3 and the inelastic torso segment 10. The torso segment 10, axillary segment 11 and end segment 4 of the arm sleeve 3 may be separate components, which when connected, form an integrated unit that limits or restricts abduction and/or external rotation of the subject's affected shoulder and/or arm, as described supra, when the shoulder stabilization apparatus is positioned and secured on a subject. In certain variations, such an effect may be achieved without the use of a separate arm, back or shoulder strap or in combination with or more of such straps.

For example, in certain variations, the inelastic, non-stretch, rigid segments or components of the shoulder stabilization apparatus, i.e., the torso segment, axillary segment and end segment of the arm sleeve, act in unison to limit or restrict abduction of a user's affected arm and/or shoulder, where abduction starts to be restricted or limited when the arm reaches about a 30 degree angle relative to the vertical mid-line of a subject. In certain variations, abduction motion starts to be restricted or limited when the arm reaches about a 45 degree angle relative to the vertical mid-line of a subject. In other variations, abduction motion is restricted or limited when the arm reaches about a 45 to 90 degree angle relative to the vertical mid-line of a subject. In certain variations, such a restriction or limitation of abduction motion may be achieved with or without the use of a separate arm, back or shoulder strap.

The shoulder stabilization apparatus 1 includes one or more accessories or straps. For example, the shoulder stabilization apparatus 1 includes an arm strap 20 and a back strap 30 for controlling or limiting certain movements or motions of the subject's shoulder and/or arm and/or stabilizing the subject's shoulder.

Figure 3:
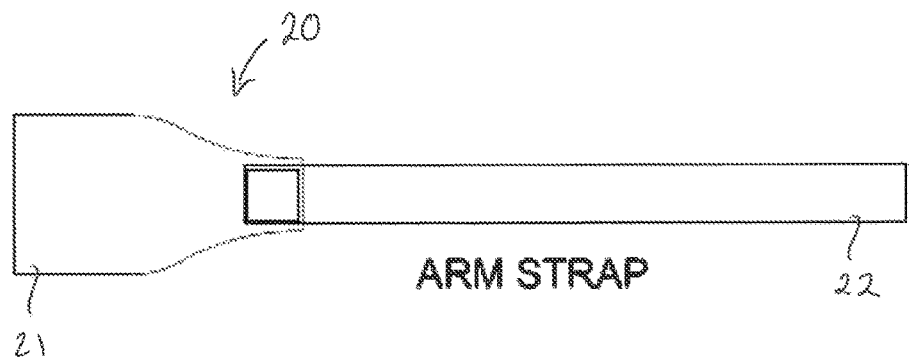
FIG. 3 illustrates an arm strap accessory for use with a shoulder stabilization apparatus.
Figure 6:
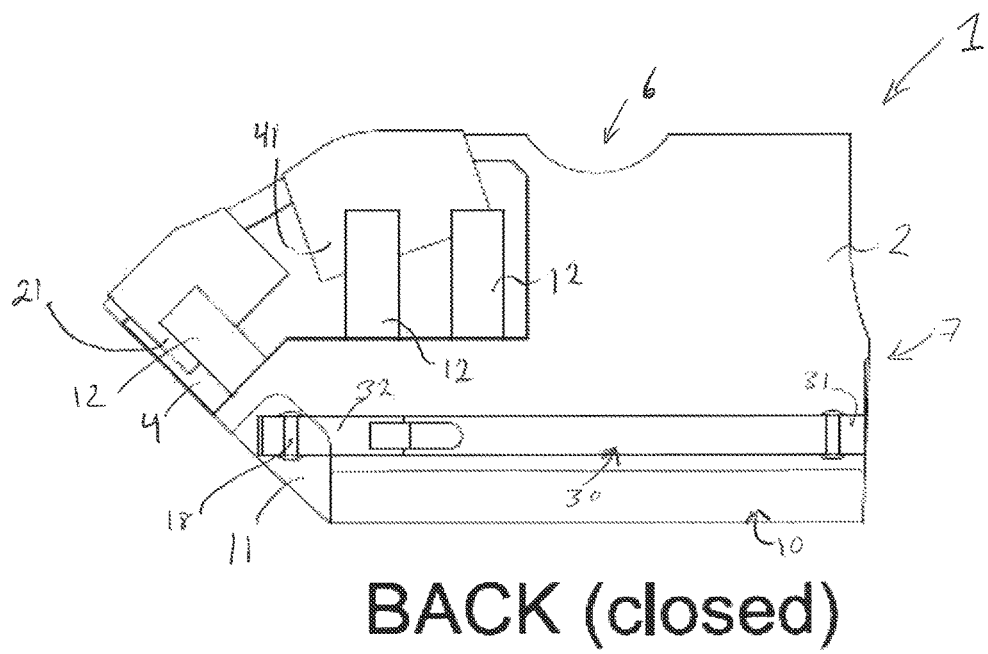
FIG. 6 illustrates a rear view of a variation of a shoulder stabilization apparatus in a closed position with an arm strap, shoulder strap and back strap secured thereto.

As shown in FIGS. 3 & 5-6, an arm strap 20 includes a first end 21, which is removably fastened or attachable to a posterior portion of the arm sleeve 3. The arm strap includes a second end 22, which is adjustably coupled to a coupling component 16, e.g., a buckle or D-ring, located on the side wrap 8. The arm strap 20 is fastened to the posterior portion of the arm sleeve 3, extends across the anterior or front portion of the torso portion 2, and is coupled or attached to the coupling component 16 on the side wrap 8 or other area of the torso portion. The tension of the arm strap 20 may be adjusted to provide the desired degree of motion control, depending on the particular subject's needs. The second end 22 of the arm strap 20 may be looped through the coupling component 16 and folded back on itself to be fastened or attached to the arm strap 20 or the torso portion 2. Once in position, the arm strap 20 limits or restricts abduction and/or external and/or internal rotation of the subject's affected shoulder and/or arm.

Figure 2:
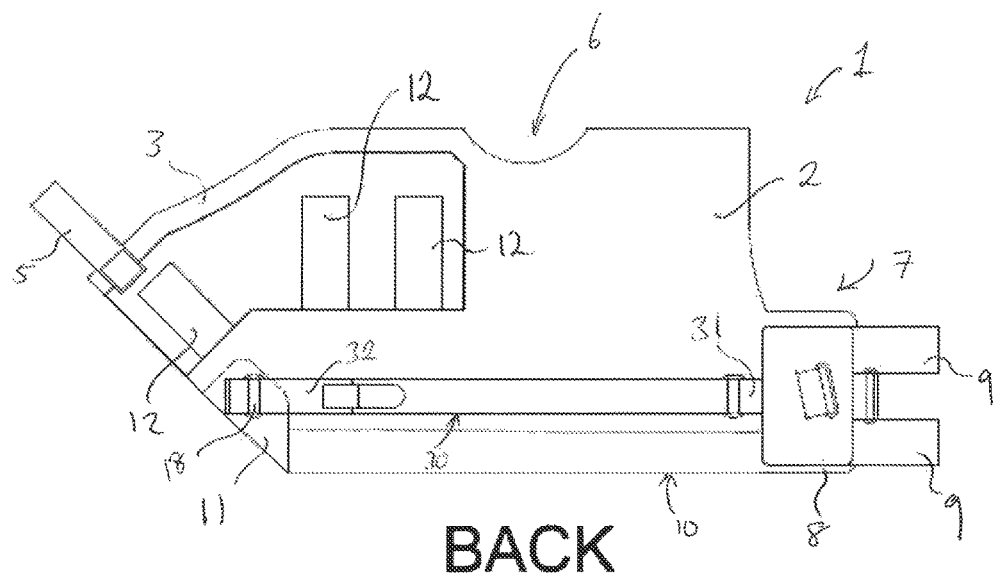
FIG. 2 illustrates a rear view of a variation of a shoulder stabilization apparatus in an open position having a back strap secured thereto.

As shown in FIGS. 2 & 6, a back strap 30 includes a first end 31, which is removably fastened or attachable to a posterior portion of the torso portion 2. The back strap 30 includes a second end 32, which is adjustably coupled to a coupling component 18, e.g., a buckle or D-ring, located on the inelastic axillary segment 11. The back strap 30 is fastened to the posterior portion of the torso portion 2, extends across the posterior or back portion of the torso portion 2, and is coupled or attached to the coupling component 18 on the inelastic axillary segment 11 or other area of the torso portion. The tension of the back strap 30 may be adjusted to provide the desired degree of motion control, depending on the particular subject's needs. The second end 32 of the back strap 30 may be looped through the coupling component 18 and folded back on itself to be fastened or attached to the back strap 30 or the torso portion 2. Once in position, the back strap 30 limits or restricts forward flexion and/or adduction of the subject's affected shoulder and/or arm.

As shown in FIGS. 2 & 6, the shoulder stabilization apparatus 1 also includes one or more anchoring straps 12 for securely fastening the arm strap 30 to the arm sleeve 3. The anchoring strap 12 has a first end affixed to a posterior portion of the arm sleeve 3 and a second end, with a fastening component on its underside, which is removably fastened to the arm strap 20. The second end of the anchoring strap 12 is pulled away from the posterior portion of the arm sleeve 3, and the first end of the arm strap 20 is positioned between the posterior portion of the arm sleeve 3 and the underside of the anchoring strap 12 or the fastening component. The anchoring strap 12 is fastened to the top surface of the first end of the arm strap 20 to provide a secure fastening of the arm strap 20 to the arm sleeve 3. Anchoring straps may also be utilized to secure the shoulder strap 40 (discussed below) to the torso portion.

Figure 4:
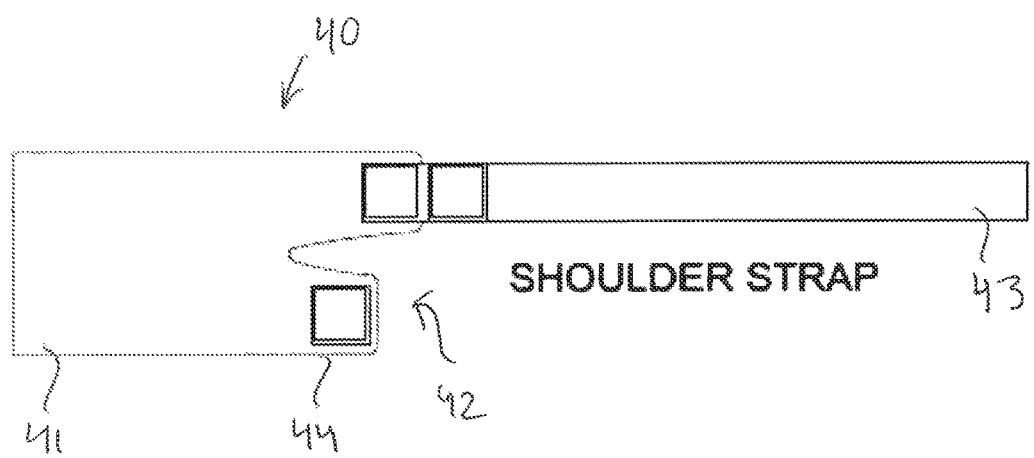
FIG. 4 illustrates a shoulder strap accessory for use with a shoulder stabilization apparatus.

As shown in FIGS. 4-6, the shoulder stabilization apparatus 1 also includes a shoulder strap 40. The shoulder strap 40 has a first end 41 which is removably fastened or attachable to a posterior portion of the torso portion 2, above the affected shoulder. The shoulder strap 40 includes a bifurcated second end 42. The bifurcated second 42 includes a first elongated segment 43 which is adjustably coupled to a coupling component 17, e.g., a buckle or D-ring, located on the side wrap 8. The bifurcated second end 42 also includes a second truncated segment 44 which is adjustably fastened or coupled to a top surface of the first elongated segment 43. The bifurcated shoulder strap first end 41 is fastened to the posterior portion of the torso portion 2, e.g., via an anchoring strap 12. The first elongated segment 43 extends across the anterior or front portion of the torso portion 2, and is coupled or attached to the coupling component 17 on the side wrap 8 or other area of the torso portion 2. The tension of the first elongated segment 43 may be adjusted to provide the desired degree of motion control, support or compression depending on the particular subject's needs. The first elongated segment 43 may be looped through the coupling component 17 and folded back on itself to be fastened or attached to the first elongated segment 43 or the torso portion 2. The second truncated segment 44 is fastened or coupled to the top surface of the first elongated element 43 e.g., folded or wrapped over it. Once in position, the shoulder strap 40 conforms, captures or contours to the affected area of the subject's shoulder, and provides support to the AC joint, restricts AC separation and/or provides compression or support of the rotator cuff of the subject's affected shoulder.

FIGS. 8-18 illustrate a step by step process for applying the shoulder stabilization apparatus 1, as described supra, to a subject and controlling or limiting motion of the subject's shoulder and/or arm and/or preventing or minimizing or stabilizing shoulder dislocation and/or subluxation. Indeed, methods for stabilizing a shoulder may include one or more of the following steps.

A shoulder stabilization apparatus 1 is provided. The shoulder stabilization apparatus 1 has a torso portion 2 and arm sleeve 3. The torso portion 2 includes a neck opening 6, a side opening 7, a side wrap 8 or extension and an inelastic and/or non-stretchable torso segment 10 surrounding a bottom periphery of the torso portion 2. The arm sleeve 3 extends from the torso portion 2. The arm sleeve 3 has an inelastic and/or non-stretchable end segment 4 and an arm sleeve fastener 5. An inelastic and/or non-stretchable axillary segment 11 forms an integrated connection between the inelastic and/or non-stretchable torso segment 10 and the inelastic and/or non-stretchable end segment 4 of the arm sleeve 3. Anchoring straps 12 are connected to the posterior portion of the torso portion 2 and arm sleeve 3.

A subject's arm is inserted into the arm sleeve 3. The arm extends from an affected or injured shoulder (or a target uninjured shoulder where the apparatus is worn as a prophylactic) that requires stabilization or restriction of motion. The subject's head and neck are inserted through the neck opening 6 and the torso portion 2 is positioned around the torso of the subject.

The torso portion 2 is secured to the subject's torso by wrapping the side wrap 8 around the side of the subject and attaching closure straps 9 to a front panel 14 on the anterior portion of the torso portion 2. This closes the side opening 7 of the torso portion 2 and secures the shoulder stabilization apparatus 1 to the subject, such that the integrated inelastic torso segment 10, inelastic axillary segment 11 and inelastic arm sleeve end segment 4 substantially limit abduction and/or external rotation of the subject's affected shoulder and/or arm.

In order to secure the arm sleeve 3 to the subject's arm, the subject flexes their bicep muscle. The subject then secures the arm sleeve fastener 5 across the slit in the distal end of the arm sleeve 3, creating a secured sleeve opening with a diameter that accommodates the subject's arm.

An arm strap 20 is then attached to the arm sleeve 3. The anchoring strap 12 is pulled away from the posterior portion of the arm sleeve 3. The first end of the arm strap 20 is then attached to the posterior portion of the arm sleeve 3. A fastening component on the underside of the first end of the arm strap 20 is fastened to the fastening component on the posterior portion of the arm sleeve 3. The anchoring strap 12 is then fastened to the top surface of the first end of the arm strap 20 providing a secure locking of the arm strap 20 to the arm sleeve 3, both above and below the arm strap 20. The arm strap 20 is extended or positioned across the anterior portion of the torso portion 2 and the second end of the arm strap 20 is passed through the coupling component 16, e.g., the buckle, located on the side wrap 8 or on the front panel. The second end of the arm strap 20 is looped through the coupling component 16 that is closest to the midline of the torso portion 2, and then folded back onto itself and pulled to achieve the desired tension. The arm strap 20 is then fastened onto itself. The secured arm strap 20 thereby limits or restricts abduction and external rotation and/or internal rotation of the subject's affected or target shoulder and/or arm.

The back strap 30, which has a first end that is fastened to a posterior portion of the torso portion 2 adjacent the side wrap 8, is then extended across the posterior portion of the torso portion 2. The second end of the back strap 30 is passed through the coupling component 18 located on the inelastic axillary component 11. The second end of the back strap 30 is looped through the coupling component 18, and then folded back onto itself and pulled to achieve the desired tension. The back strap 30 is then fastened onto itself. The secured back strap thereby limits forward flexion and adduction of a subject's affected or target shoulder and/or arm.

Additionally, or alternatively, a bifurcated shoulder strap 40 may then be attached to the torso portion 2. The anchoring strap 12 is pulled away from the posterior portion of the torso portion 2. The first end of the shoulder strap 40 is then attached to the posterior portion of the torso portion 2. A fastening component on the underside of the first end of the shoulder strap 40 is fastened to the fastening component on the posterior portion of the torso portion 2. The anchoring strap 12 is then fastened to the top surface of the first end of the shoulder strap 40 providing a secure locking of the shoulder strap 40 to the torso portion 2, both above and below the shoulder strap 40. The first elongated segment 43 of the bifurcated shoulder strap 40 extends across the anterior or front portion of the torso portion 2, and is coupled or attached to the coupling component on the side wrap 8. The first elongated segment 43 is passed through the coupling component 17, e.g., the buckle, located on the side wrap 8 or on the front panel. The elongated segment 43 is looped through the coupling component 17, and then folded back onto itself and pulled to achieve the desired tension. The elongated segment is then fastened onto itself. The second truncated segment 44 is adjusted fastened or coupled to the top surface of the first elongated element 43 e.g., folded or wrapped over it. The secured shoulder strap 40 conforms, captures or contours to the affected or target area of the subject's shoulder, and thereby provides support to the AC joint, restricts AC separation and/or provides compression of the rotator cuff of the subject's affected or targeted shoulder.

The above described apparatus and straps may limit or restrict various types of movement, e.g., the various types of movement described herein, but still afford flexibility and allow for movement of other areas of the body such that a subject can continue to partake in athletic and other activities, safely, while wearing the apparatus. The straps can be fine-tuned and adjusted, providing adjustability based on the strapping sequence and tension applied to suit a subject's needs. The shoulder stabilization apparatus can be customized to the unique mechanism of instability for a particular subject and provide balancing to the subject's shoulder and customize a customized fit. The apparatus is designed to control and stabilize combined instability or multidirectional instability, e.g., anterior and/or posterior directional instability and/or AC separation. In certain variations, the arm strap and shoulder strap may couple to either coupling component 16 or 17.

The shoulder stabilization apparatus, e.g., the inelastic and/or non-stretchable segments of the torso portion, axillary segment and arm sleeve, alone, where the arm strap, back strap and shoulder strap are not utilized, can limit varying degrees of abduction or extreme abduction, and external rotation. For example, restriction of abduction may begin at about 30 degrees, and based on variability of soft tissue may have an endpoint at about 90 degrees, relative to the longitudinal or vertical axis or midline of the patient. The endpoint may be greater than 90 degrees. Some external rotation may be restricted via arm sleeve friction alone acting on the arm.

Figure 7:
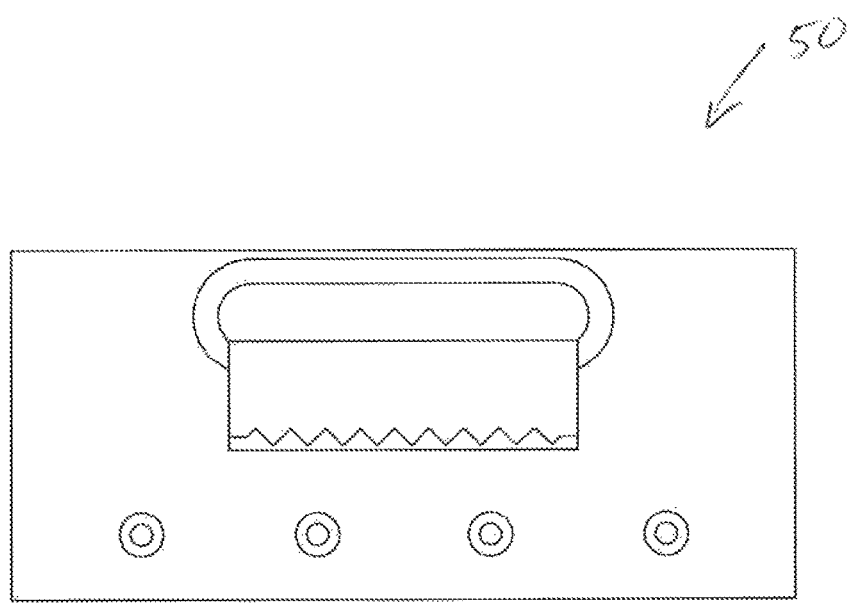
FIG. 7 illustrates a shoulder pad lacer accessory for attaching an arm strap to a shoulder pad assembly.
Figure 8:
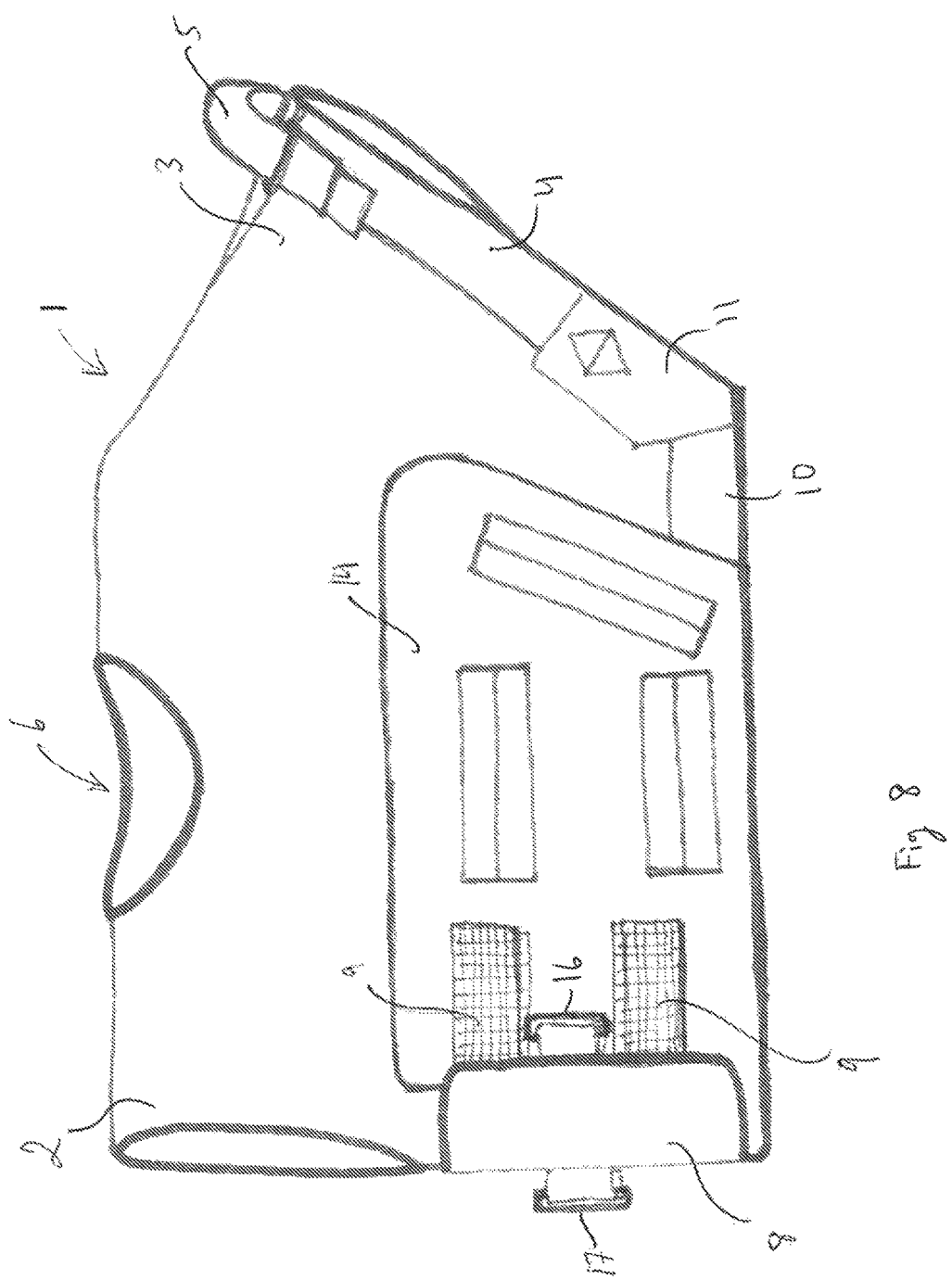
FIGS. 8-18 illustrate a step by step process for applying a shoulder stabilization apparatus to a subject.
Figure 9:
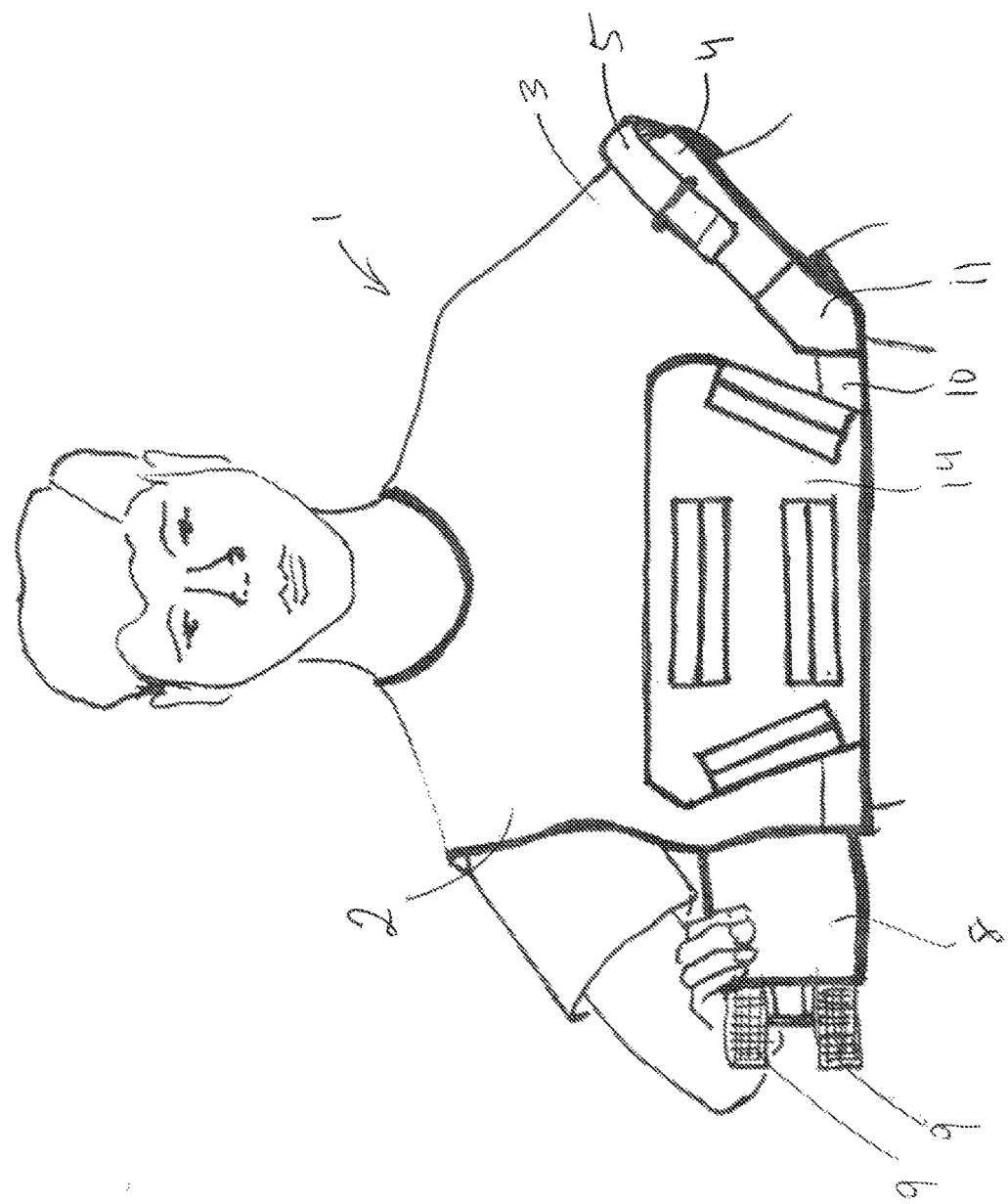
Figure 10:
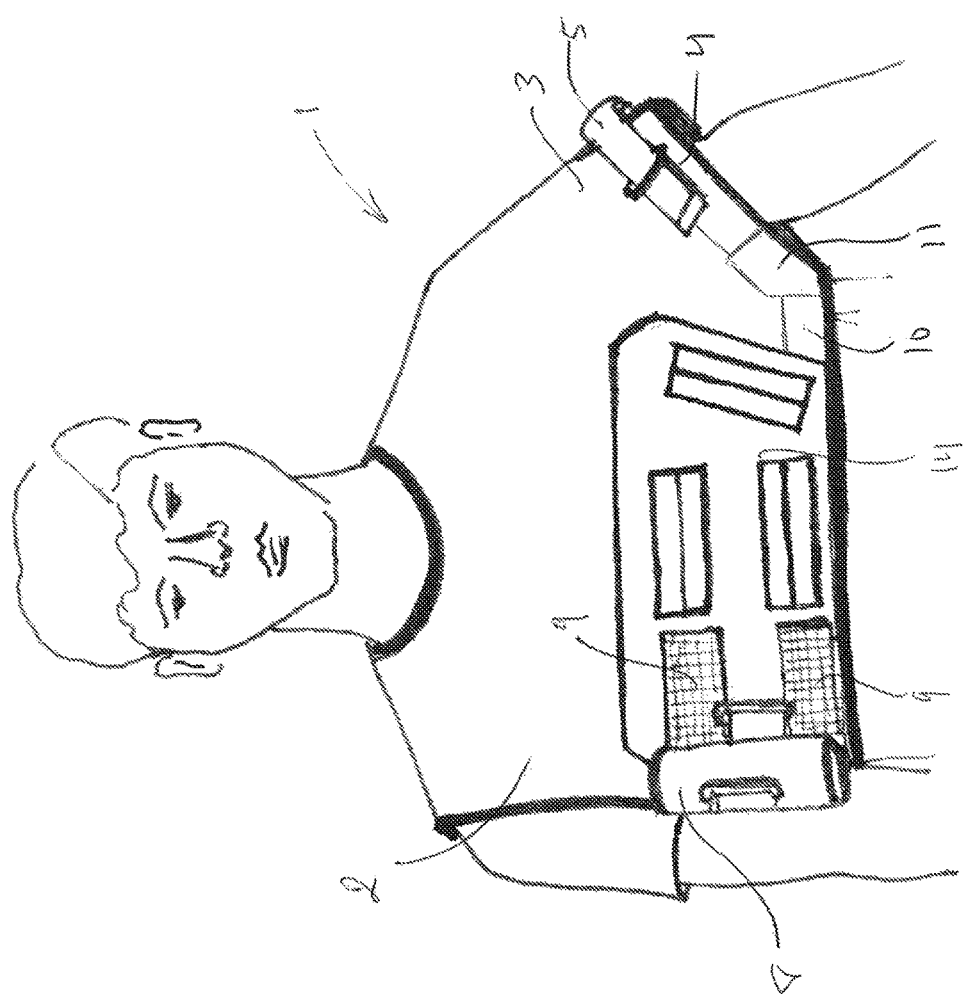
Figure 11:
Figure 12:
Figure 13:
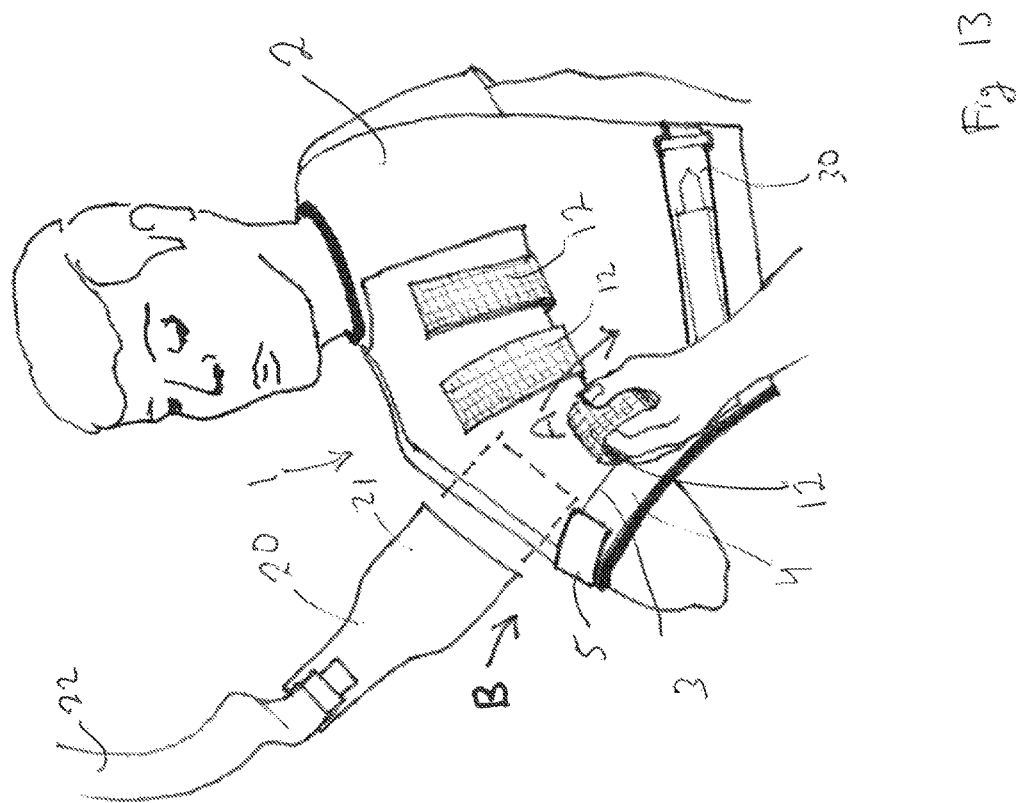
Figure 14:
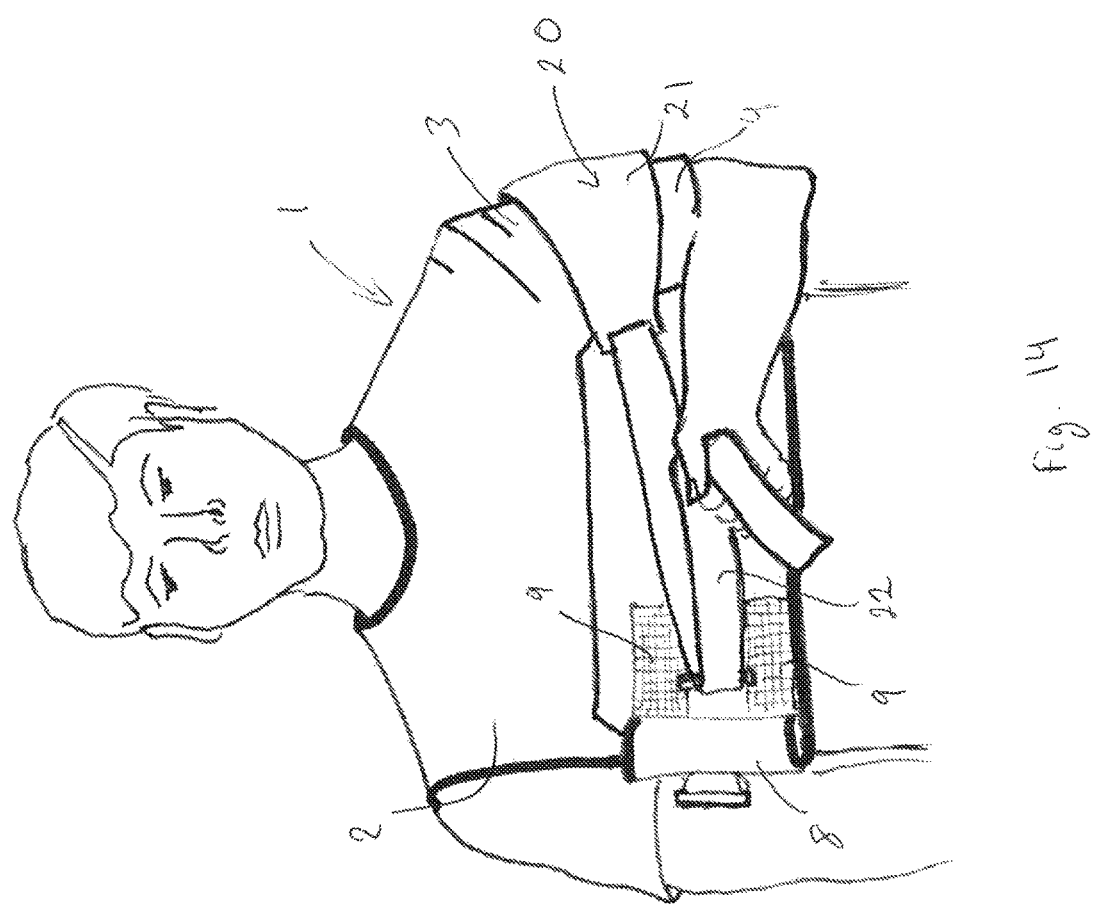
Figure 19:
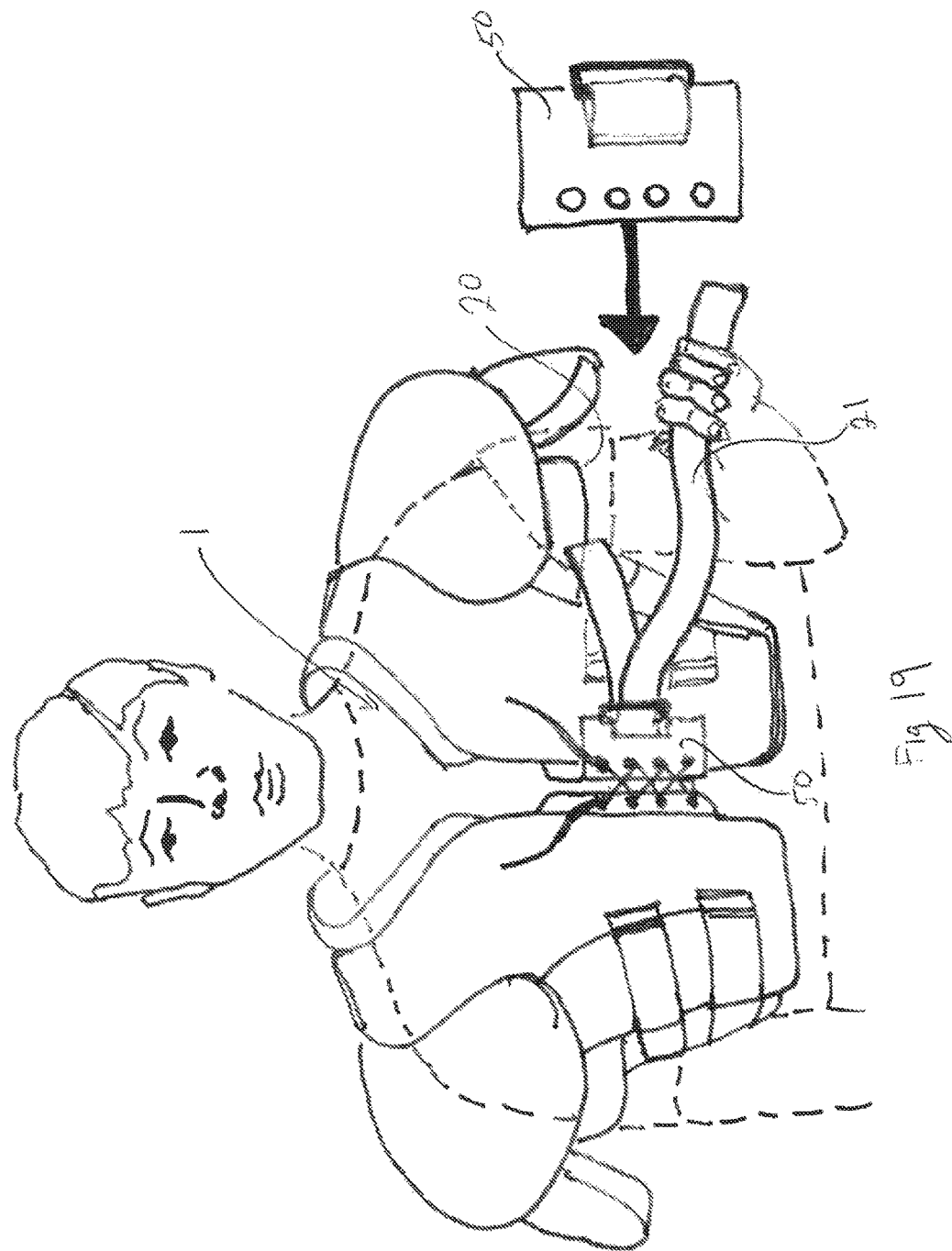
FIGS. 19-20 illustrate a shoulder stabilization apparatus connected to a shoulder pad assembly via a shoulder pad lacer accessory.
Figure 20:
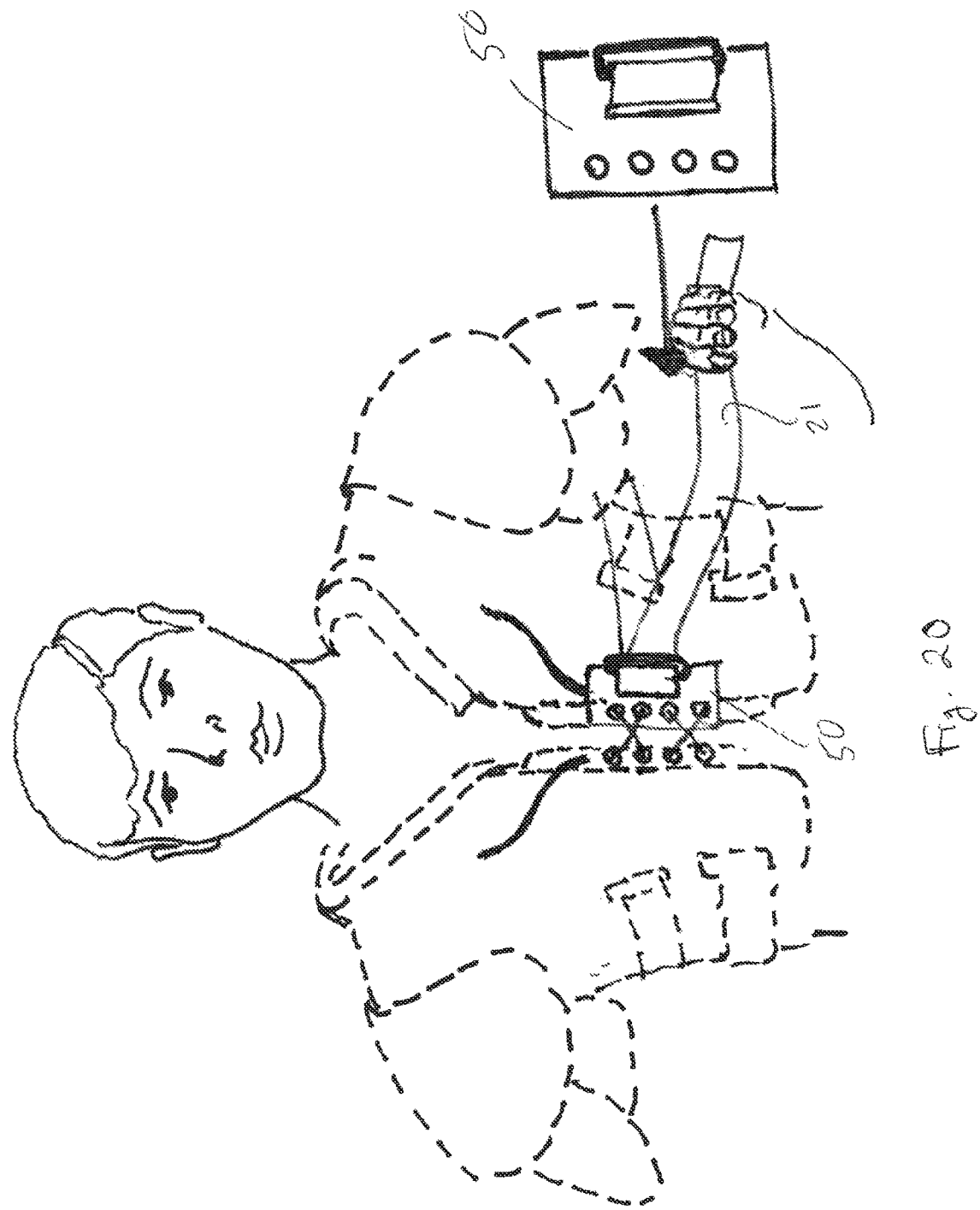
Figure 21:
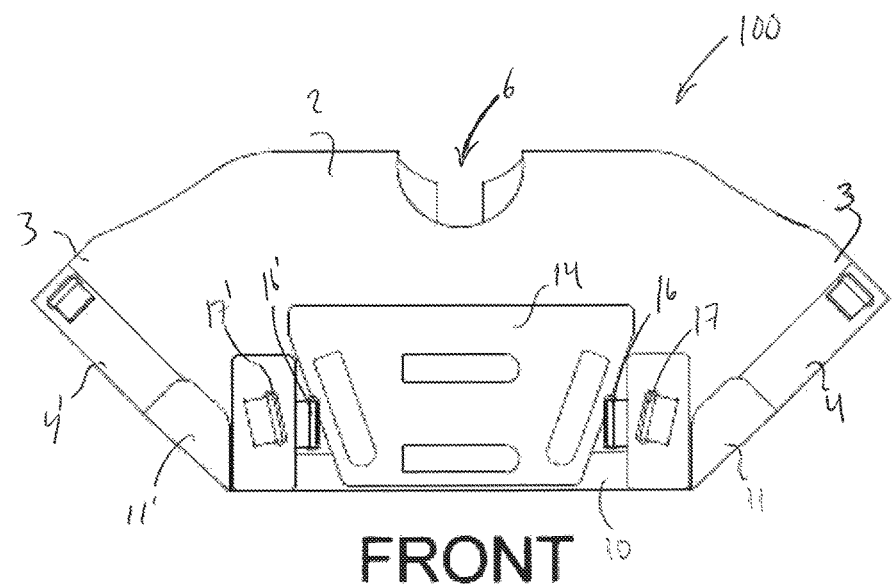
FIG. 21 illustrates a front view of a bilateral variation of a shoulder stabilization apparatus in an open position.
Figure 22:
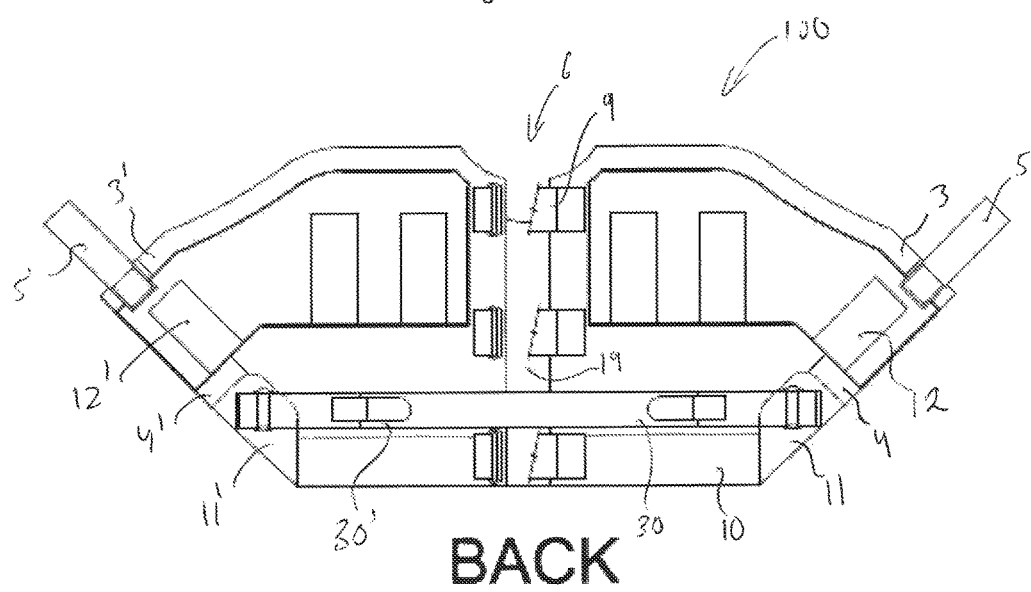
FIG. 22 illustrates a rear view of a bilateral variation of a shoulder stabilization apparatus in an open position having a back straps secured thereto.

FIGS. 7 and 19-20 illustrate another variation of a shoulder stabilization apparatus which is connected to a shoulder pad assembly 60 via a shoulder pad lacer accessory 50. A shoulder stabilization apparatus 1, according to any of the variations or embodiments described herein, may include a shoulder pad lacing accessory 50. The shoulder pad lacing accessory 50 has one or more coupling components 51, e.g., a buckle or D-ring, and is configured to be laced directly to a shoulder pad assembly 60 via the shoulder pad assembly's lacing. The arm strap 20 includes a first end 21, which is removably fastened or attached to a posterior portion of the arm sleeve 3. The arm strap includes a second end 22, which is adjustably coupled to the coupling component 51, e.g., a buckle or D-ring, located on the shoulder pad lacing accessory 50, which is attached to the shoulder pad assembly 60. As such, the arm strap 20 is fastened to the posterior portion of the arm sleeve 3, extends across and over the anterior or front portion of the shoulder pad assembly 60, and is coupled or attached to the coupling component 51 on the shoulder pad lacing accessory 50. Once in position, the arm strap 20 limits abduction and/or external rotation of the subject's affected shoulder and/or arm, while the subject is wearing a shoulder pad assembly and is still able to partake in a sporting activity requiring shoulder pads, e.g., football or hockey.

Figure 23:
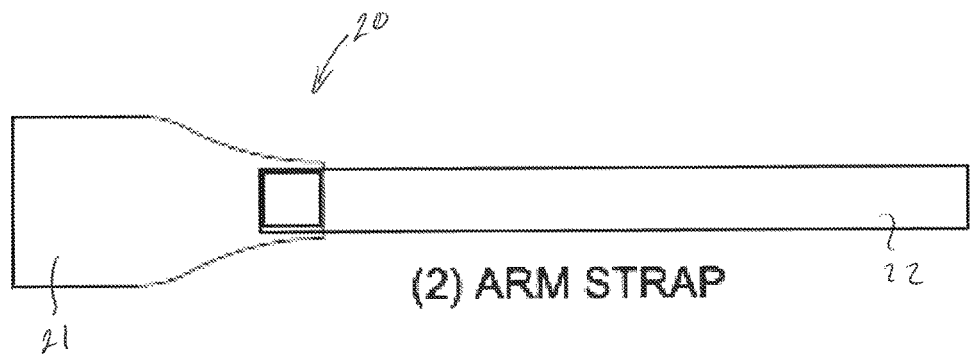
FIG. 23 illustrates an arm strap accessory for use with a bilateral variation of a shoulder stabilization apparatus.
Figure 24:
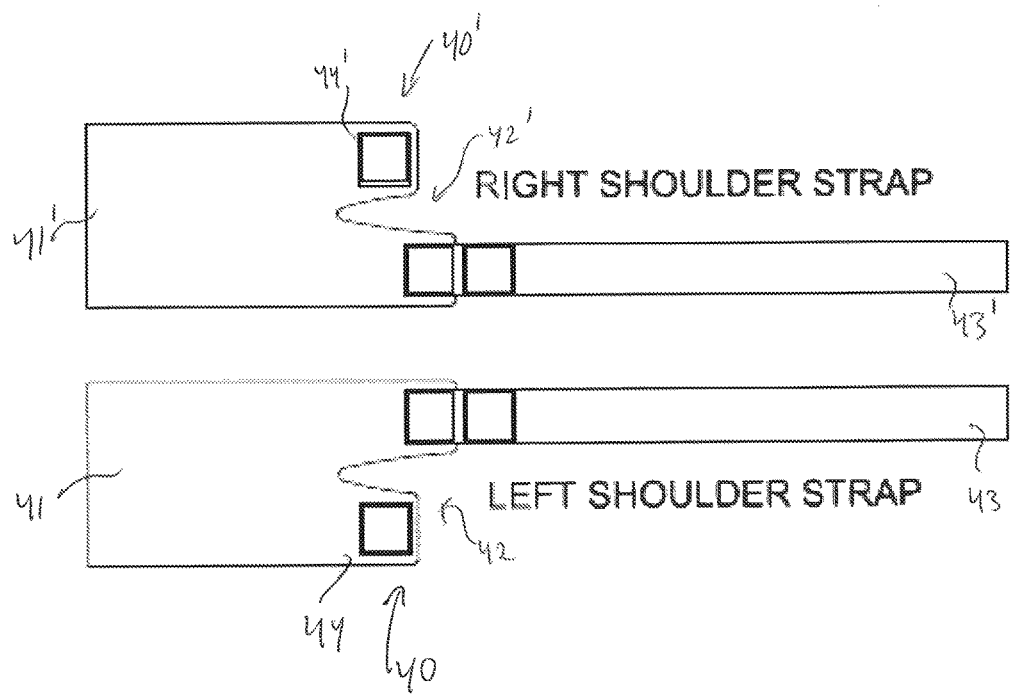
FIG. 24 illustrates left and right shoulder strap accessories for use with a bilateral variation of a shoulder stabilization apparatus.
Figure 25:
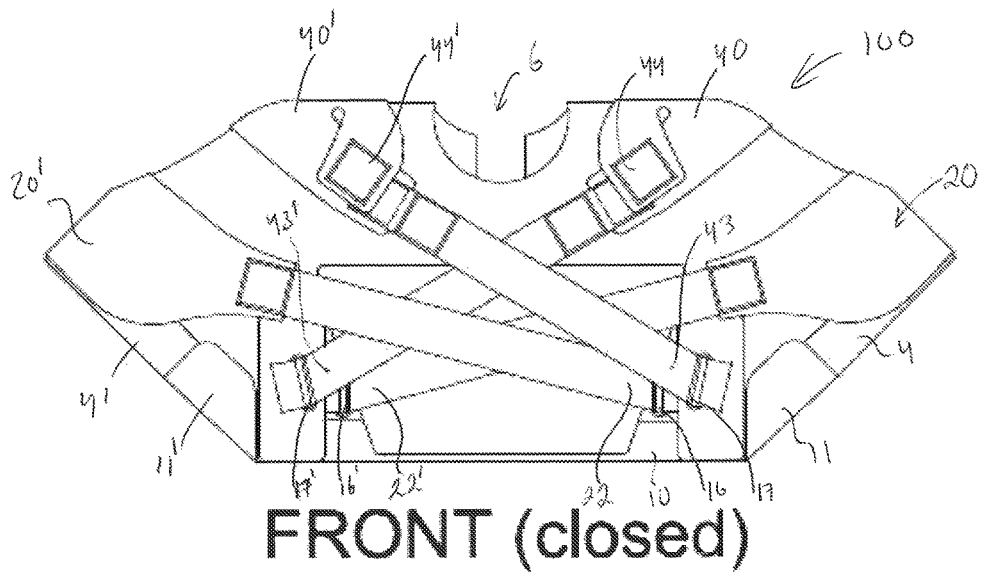
FIG. 25 illustrates a front view of a bilateral variation of a shoulder stabilization apparatus in a closed position with two arm straps and left and right shoulder straps secured thereto.
Figure 26:
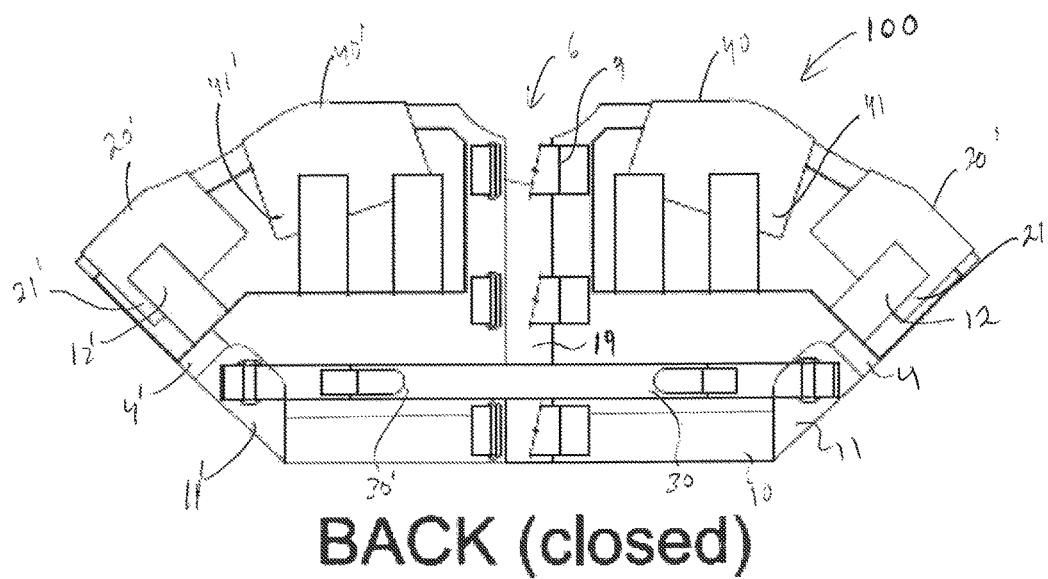
FIG. 26 illustrates a rear view of a bilateral variation of a of a shoulder stabilization apparatus in a closed position with two arm straps, left and right shoulder straps and two back straps secured thereto.

In an alternative variation, the shoulder stabilization apparatus may be bilateral, having an inelastic and/or non-stretchable torso segment 10 two inelastic and/or non-stretchable axillary segments 11, 11' and two arm sleeves 3, 3' with inelastic and/or non-stretchable segments extending from the torso portion to accommodate both the left and right shoulder and/or arms of a subject. FIGS. 21-22 and 25-26 illustrate front and rear views of a bilateral variation of a shoulder stabilization apparatus 100 in an opened and closed position with two arm straps 20, 20', left and right shoulder straps 40, 40' and two back straps 30, 30' secured thereto. FIGS. 23-24 illustrate an arm strap 20 (two or more arm straps may be utilized in the bilateral shoulder stabilization apparatus), and left and right shoulder straps 40, 40'. The bilateral shoulder stabilization apparatus 100 includes features identical to the features described with respect to the unilateral shoulder stabilization apparatus 1 as described above. The bilateral shoulder stabilization apparatus 100 operates in the same manner as the unilateral shoulder stabilization apparatus 1 as described above, but allows for restriction or limitation of movement of both the left and right shoulder's and/or arms of a subject. Also, the bilateral shoulder stabilization apparatus 100 may have a back opening 19, which is opened in order to position or slip the apparatus on a subject's body, and then closed with closure straps 9 to secure it thereon, e.g., instead of having a side opening and side wrap. The features/elements of the bilateral shoulder stabilization apparatus 100 illustrated in FIGS. 21-26 include the same element numbering as used to identify the identical features/elements in the unilateral shoulder stabilization apparatus 1 illustrated in FIGS. 1-2 and 5-6, with the addition of a second set of corresponding element numbers to identify the duplicative or mirrored second element of a pair of elements for those elements that are duplicated on the bilateral shoulder stabilization apparatus. For example, 3 and 3' are used to represent the left and right arm sleeves, and so on.

For example, the bilateral shoulder stabilization apparatus 100 may be opened at back opening 19 and slipped on a subject where each arm is slipped through each arm sleeve 3, 3'. The closure straps 9 may be secured to close the back opening and the arm sleeve fastener's 4, 4' may be secured to fit the arm sleeve around the arm of the particular subject. One or more arm straps 20, 20', may be fastened to the posterior portion of each arm sleeve and extended across the anterior of the torso portion 2 and coupled to coupling components 16, 16', as described supra. One or more back straps 30, 30', may be fastened to a posterior portion of the torso portion, and extended across the posterior or back portion of the torso portion, and coupled to coupling components 18, 18' on or adjacent to the inelastic axillary segments or other area of the torso portion, as described supra. One or more shoulder straps 40, 40', may be fastened to the posterior portion of the torso portion, one each of the left and right sides of the torso, and extended across the anterior of the torso portion 2 and coupled to coupling components 17, 17', as described supra. This provides customizable stabilization and/or support to both of a subject's shoulders and/or arms.

Alternatively, in certain variations, one or more axillary segments may be adjustable.

In another variation, one or more buttresses may be coupled to the torso portion, to serve as a training device to remind the user to limit motion of their arm when their arm hits or comes into contact with the buttress. The location of the buttress on the stabilization apparatus is dependent on the instability of the shoulder and what is being treated. Examples of locations where a buttress may originate from or be positioned include but are not limited to: the axilla (anterior or posterior). For example, the buttress may extend from the anterior chest laterally toward the axilla.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A shoulder stabilization apparatus comprising:
   a torso portion having a neck opening, a side opening, a side wrap and an inelastic and/or non-stretchable torso segment surrounding a bottom periphery of the torso portion;
   an arm sleeve extending from the torso portion, wherein the arm sleeve has an inelastic and/or non-stretchable end segment, the arm sleeve being configured to receive a subject's arm, the arm extending from an affected or target shoulder;
   an inelastic and/or non-stretchable axillary segment forming an integrated connection between the torso segment and the arm sleeve end segment, which limits abduction and/or external rotation of the subject's affected or target shoulder and/or arm;
   an arm strap, wherein the arm strap has a first end configured to be removably fastened to a posterior portion of the arm sleeve, the arm strap extending across an anterior portion of the torso portion and having a second end configured to be adjustably coupled to a coupling component located on the side wrap, such that the arm strap limits abduction and/or external rotation of the subject's affected or target shoulder and/or arm; and
   a back strap, wherein the back strap has a first end configured to be removably fastened to a posterior portion of the torso portion, the back strap extending across a posterior portion of the torso portion and having a second end configured to be adjustably coupled to a coupling component located on the inelastic and/or non-stretchable axillary segment, such that the back strap limits forward flexion and/or adduction of the subject's affected or target shoulder and/or arm.

2. The shoulder stabilization apparatus according to claim 1, further comprising one or more closure straps, wherein the closure straps have a first end affixed to the side wrap and a second end configured to be removably fastened to an anterior portion of the torso portion to secure the torso portion to the subject.

3. The shoulder stabilization apparatus according to claim 1, wherein the inelastic and/or non-stretchable segments surrounding the bottom periphery of the torso portion and the arm sleeve include a gripping surface to prevent sliding of the torso portion and arm sleeve on the subject.

4. The shoulder stabilization apparatus according to claim 1, wherein the arm sleeve is adjustable to accommodate a variety of arm sizes.

5. The shoulder stabilization apparatus according to claim 4, wherein the arm sleeve has an adjustable slit at its distal end adjacent an arm opening, and one or more arm sleeve fasteners, wherein the arm sleeve fasteners have a first end affixed to first side of the slit and a second end configured to be removably fastened to a second side of the slit, such that the arm sleeve fastener changes the diameter of the slit and the size of arm opening depending on its placement.

6. The shoulder stabilization apparatus according to claim 1, further comprising one or more anchoring straps, wherein the anchoring strap has a first end affixed to a posterior portion of the arm sleeve and a second end configured to be removably fastened to the arm strap.

7. The shoulder stabilization apparatus according to claim 6, wherein the second end of the anchoring strap is configured to be pulled away from the posterior portion of the arm sleeve such that the first end of the arm strap can be positioned between the posterior portion of the arm sleeve and an underside of the anchoring strap, wherein the second end of the anchoring strap is fastened to a top surface of the first end of the arm strap to provide a secure fastening of the arm strap to the arm sleeve.

8. The shoulder stabilization apparatus according to claim 1, wherein the first end of the arm strap has a hook or loop fastening component which is configured to fasten to a hook or loop fastening component positioned on a posterior portion of the arm sleeve.

9. The shoulder stabilization apparatus according to claim 1, wherein the arm strap is configured to extend only across the anterior portion of the torso portion without extending across a posterior portion of the torso portion.

10. The shoulder stabilization apparatus according to claim 1, wherein at least a portion of the arm strap is elastic to provide give or flexibility, allowing for limited external rotation and/or abduction of the subject's affected or target shoulder and/or arm.

11. The shoulder stabilization apparatus according to claim 1, further comprising a shoulder strap, wherein the shoulder strap has a first end configured to be removably fastened to a posterior portion of the torso portion above the affected or target shoulder, wherein the shoulder strap has a bifurcated second end having a first elongated segment which is configured to be adjustably coupled to a coupling component located on the side wrap, and a second truncated segment which is configured to be adjustably coupled to a top surface of the first elongated segment, the shoulder strap extending across an anterior portion of the torso portion, such that the shoulder strap provides support to the AC joint, restricts AC separation and/or provides compression of the rotator cuff of the subject's affected or target shoulder.

12. The shoulder stabilization apparatus according to claim 11, wherein the first elongated segment of the shoulder strap is extended only across the anterior portion of the torso portion without extending across a posterior portion of the torso portion.

13. The shoulder stabilization apparatus according to claim 11, wherein at least a portion of the shoulder strap is elastic, providing give such that the shoulder strap contours to the affected area of the subject's shoulder.

14. A method of stabilizing a shoulder of a subject comprising:
providing a shoulder stabilization apparatus, wherein the shoulder stabilization apparatus has a torso portion having a neck opening, a side opening, a side wrap and an inelastic and/or non-stretchable torso segment surrounding a bottom periphery of the torso portion, an arm sleeve extending from the torso portion wherein the arm sleeve has an inelastic and/or non-stretchable end segment; and an inelastic and/or non-stretchable axillary segment forming an integrated connection between the torso segment and the end segment;
inserting a subject's arm, the arm extending from an affected or target shoulder, through the arm sleeve and inserting the subject's head through the neck opening;
attaching the side wrap to an anterior portion of the torso portion thereby closing the side opening of the torso portion and securing the shoulder stabilization apparatus to the subject, such that the integrated inelastic and/or non-stretchable torso segment, axillary segment and end segment limit abduction and/or external rotation of the subject's affected or target shoulder and/or arm;
providing an arm strap, wherein the arm strap has a first end and a second end;
fastening the first end to a posterior portion of the arm sleeve, extending the arm strap across an anterior portion of the torso portion and attaching a second end of the arm strap to a coupling component located on the side wrap, thereby limiting abduction and/or external rotation of the subject's affected or target shoulder and/or arm;
providing a back strap, wherein the back strap has a first end and a second end; and
fastening the first end to a posterior portion of the torso portion, extending the back strap across a posterior portion of the torso portion and attaching a second end of the back strap to a coupling component located on the inelastic and/or non-stretchable axillary segment, thereby limiting forward flexion and/or adduction of the subject's affected or target shoulder and/or arm.

15. The method according to claim 14, wherein the shoulder stabilization apparatus
prevents shoulder dislocation or subluxation.

16. The method according to claim 14, further comprising providing one or more closure
straps extending from the side wrap and removably fastening the closure straps to an anterior portion of the torso portion to secure the torso portion to the subject.

17. The method according to claim 14, wherein the inelastic and/or non-stretchable
segments surrounding the bottom periphery of the torso portion and the arm sleeve include a gripping surface to prevent sliding of the torso portion and arm sleeve on the subject.

18. The method according to claim 14, wherein the arm sleeve is adjustable to
accommodate a variety of arm sizes.

19. The method according to claim 18, wherein the arm sleeve has an adjustable slit at its distal end adjacent an arm opening, and one or more arm sleeve fasteners, wherein the arm sleeve fasteners have a first end affixed to first side of the slit and a second end configured to be removably fastened to a second side of the slit, such that the arm sleeve fastener changes the diameter of the slit and the size of arm opening depending on its placement.

20. The method according to claim 14, further comprising one or more anchoring straps,
wherein the anchoring strap has a first end affixed to a posterior portion of the arm sleeve and a second end configured to be removably fastened to the shoulder strap to provide a secure fastening of the arm strap to the torso portion.

21. The method according to claim 14, wherein the first end of the arm strap has a hook or loop fastening component which is configured to fasten to a hook or loop fastening component positioned on a posterior portion of the torso portion.

22. The method according to claim 14, further comprising:
providing a shoulder strap, wherein the shoulder strap has a first end configured to be removably fastened to a posterior portion of the torso portion above the affected or target shoulder, wherein the shoulder strap has a bifurcated second end having a first elongated segment which is configured to be adjustably coupled to a coupling component located on the side wrap, and a second truncated segment which is configured to be adjustably coupled to a top surface of the first elongated segment;
extending the first elongated segment and the second truncated segment across an anterior portion of the torso portion, such that the shoulder strap provides support to the AC joint, restricts AC separation and/or provides compression of the rotator cuff of the subject's affected or target shoulder.

23. The method according to claim 22, wherein the first elongated segment of the shoulder strap is extended only across the anterior portion of the torso portion without extending across a posterior portion of the torso portion.

24. The method according to claim 14, wherein at least a portion of the arm strap is elastic, providing give or flexibility, allowing for limited external rotation and/or abduction of the subject's affected or target shoulder and/or arm.

25. The method according to claim 14, wherein the shoulder stabilization apparatus is secured by the subject wearing the apparatus without the assistance of a second person.

* * * * *